US011585493B2

(12) United States Patent
Medricky

(10) Patent No.: US 11,585,493 B2
(45) Date of Patent: Feb. 21, 2023

(54) LED LIGHTING SOURCE FOR IMPROVED COGNITIVE PERFORMANCE AND WITH SUN-LIGHT PROPERTIES

(71) Applicants: Hynek Medricky, Prague (CZ); Daniel Jesensky, Prague (CZ); Daniel Stepan, Prague (CZ)

(72) Inventor: Hynek Medricky, Prague (CZ)

(*) Notice: Subject to any disclaimer, the term of this patent is extended or adjusted under 35 U.S.C. 154(b) by 0 days.

(21) Appl. No.: 17/257,210

(22) PCT Filed: Jul. 3, 2019

(86) PCT No.: PCT/IB2019/055694
§ 371 (c)(1),
(2) Date: Dec. 30, 2020

(87) PCT Pub. No.: WO2020/008397
PCT Pub. Date: Jan. 9, 2020

(65) Prior Publication Data
US 2021/0164624 A1    Jun. 3, 2021

(30) Foreign Application Priority Data
Jul. 3, 2018  (CS) .................................. CZ2018-330

(51) Int. Cl.
*F21K 9/64*    (2016.01)
*H05B 45/20*   (2020.01)
*A61N 5/06*    (2006.01)

(52) U.S. Cl.
CPC .............. *F21K 9/64* (2016.08); *A61N 5/0618* (2013.01); *H05B 45/20* (2020.01); *A61N 2005/0652* (2013.01); *A61N 2005/0663* (2013.01)

(58) Field of Classification Search
CPC .......... A61N 5/0618; A61N 2005/0652; A61N 2005/0663; H05B 45/20
See application file for complete search history.

(56) References Cited

U.S. PATENT DOCUMENTS

| 7,135,664 B2* | 11/2006 | Vornsand | H05B 45/22 250/205 |
| 2009/0200907 A1* | 8/2009 | Zukauskas | H05B 45/20 313/1 |

(Continued)

OTHER PUBLICATIONS

Cree, Cree XLamp XHP35 LEDs, Product Family Data Sheet, 2018 (Year: 2018).*

*Primary Examiner* — Keith G. Delahoussaye
(74) *Attorney, Agent, or Firm* — Cionca IP Law P.C.; Marin Cionca

(57) ABSTRACT

A subject of the invention is the source of LED lighting that improves human cognitive performance during work activities or in any activity and simulates sun radiation in the biologically beneficial range 460 to 660 nm, for more than 90%. The whole system of the LED lighting source is set in such a way that 4.5 to 6% of blue and turquoise light radiation is added to the light radiation emitted from white LED chips, and it is advantageous if of equal radiation intensity. This measurement will provide for balancing of radiation intensity to 90% of the sunshine level. The generated combined light radiation of the cognitive LED lighting source has CRI 98 and correlated colour temperature 4000 to 4700 K, the sun radiation has correlated colour temperature 4982 K and CRI 99.5.

14 Claims, 23 Drawing Sheets

(56) References Cited

U.S. PATENT DOCUMENTS

2014/0055041 A1* 2/2014 Ramer ................. H05B 47/175
  315/153
2017/0135176 A1* 5/2017 Soler ...................... H05B 45/24
2017/0343168 A1* 11/2017 Ting ....................... A01G 33/00

* cited by examiner

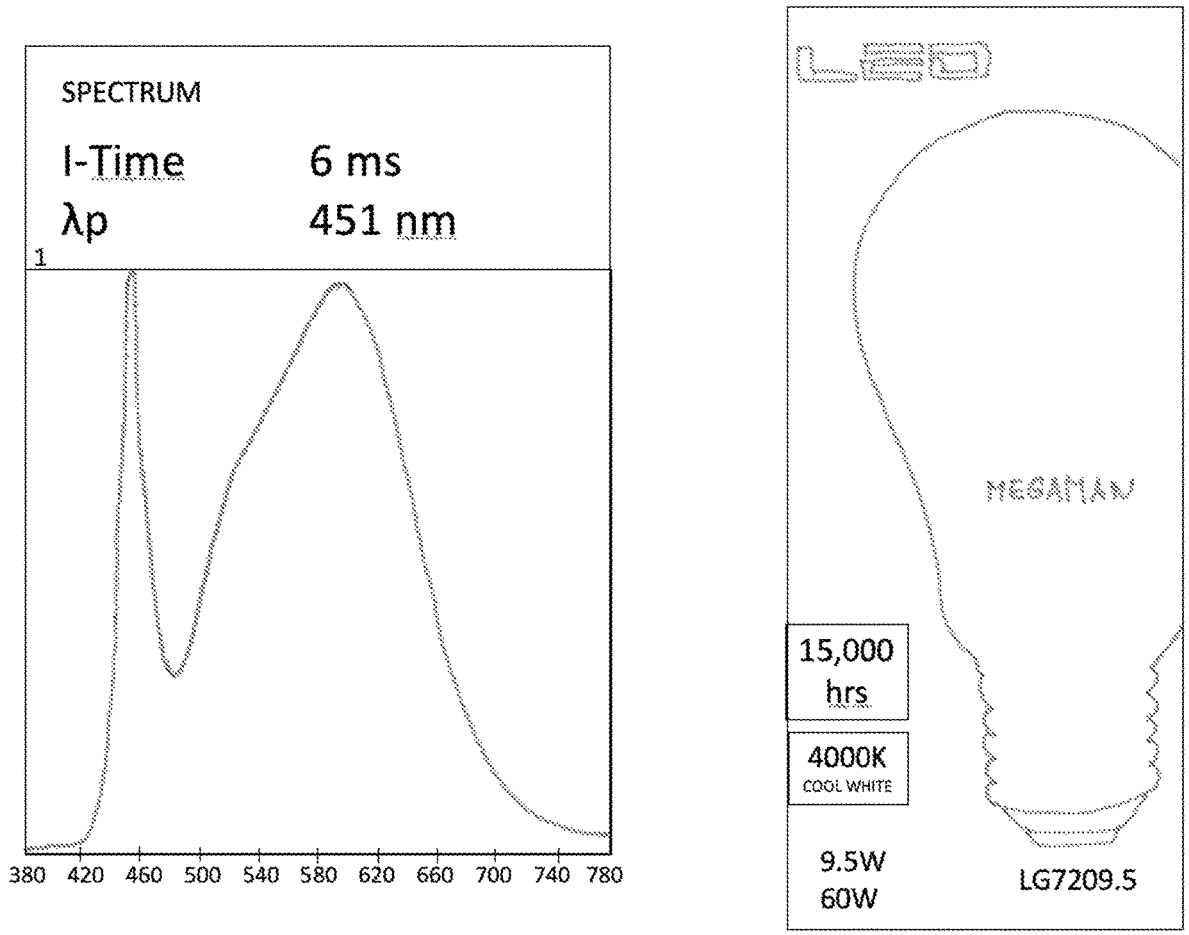
Fig. 2 - Prior Art

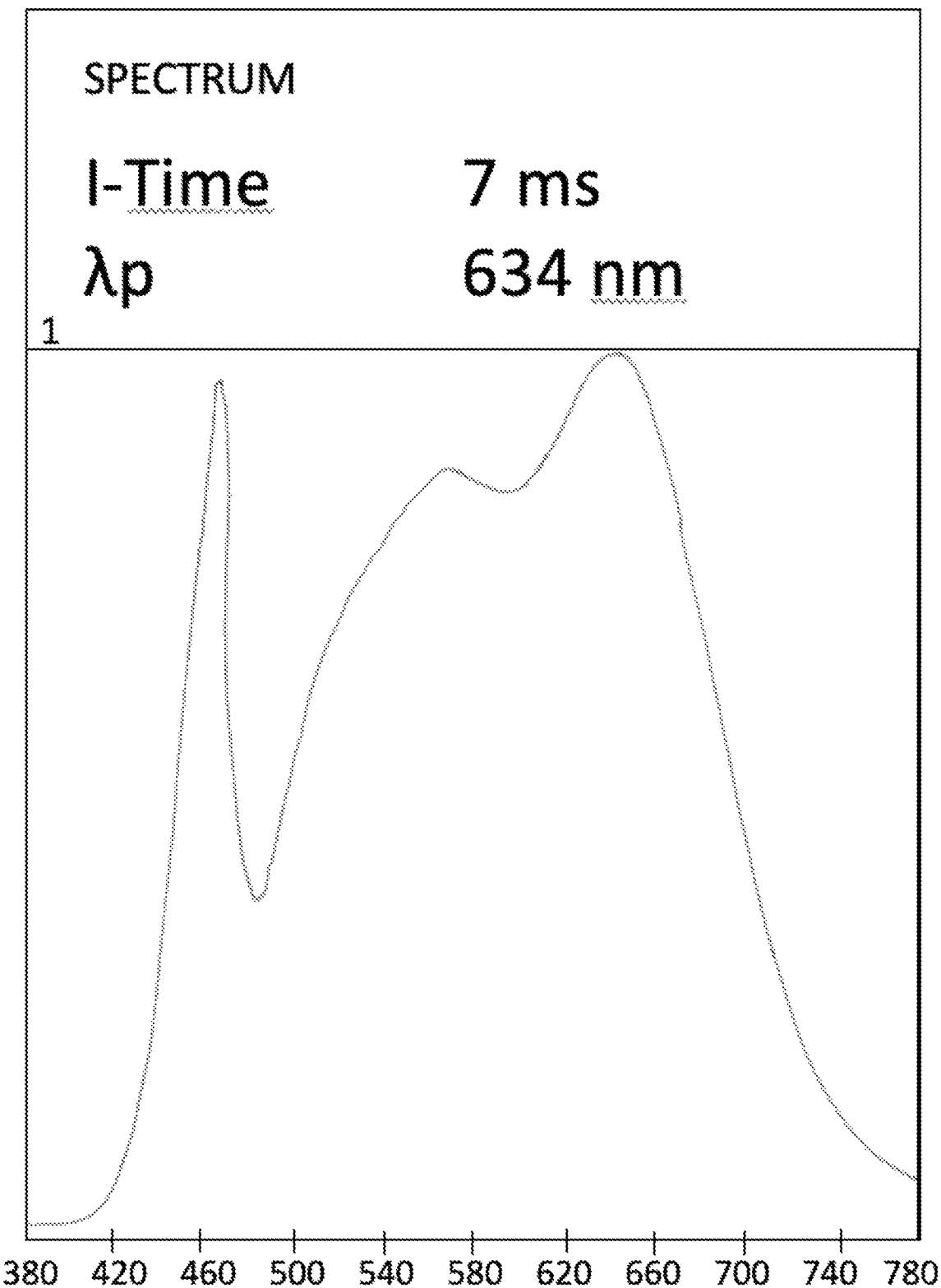
Fig. 3 - Prior Art

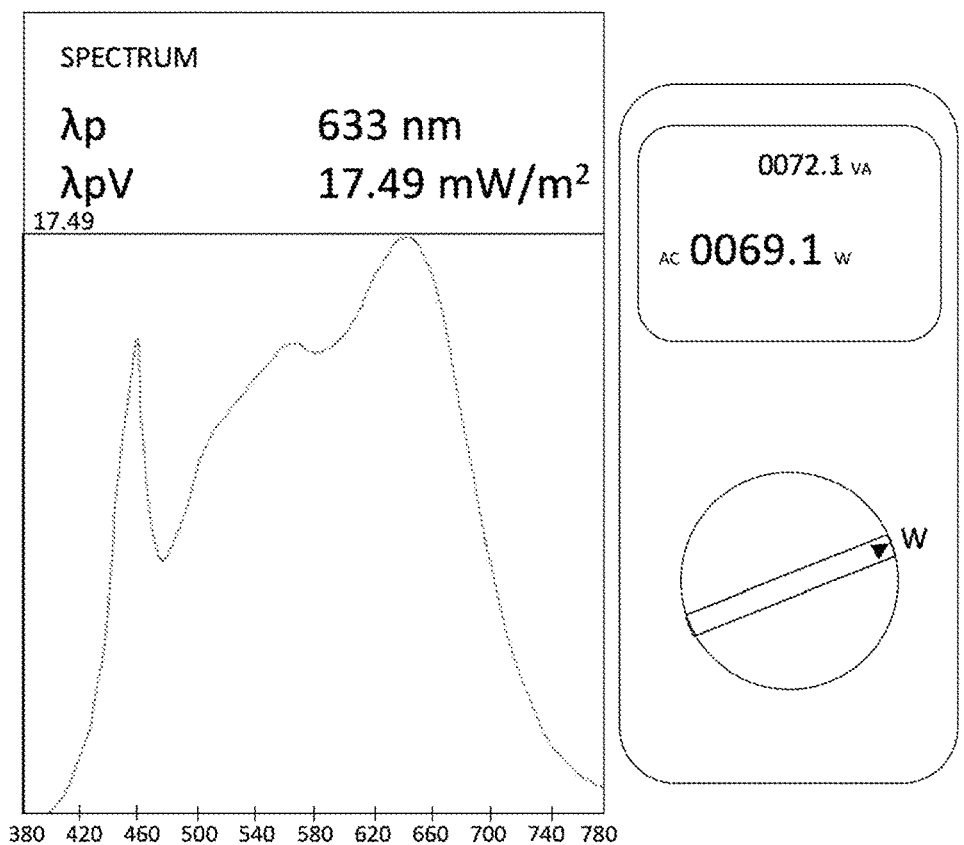
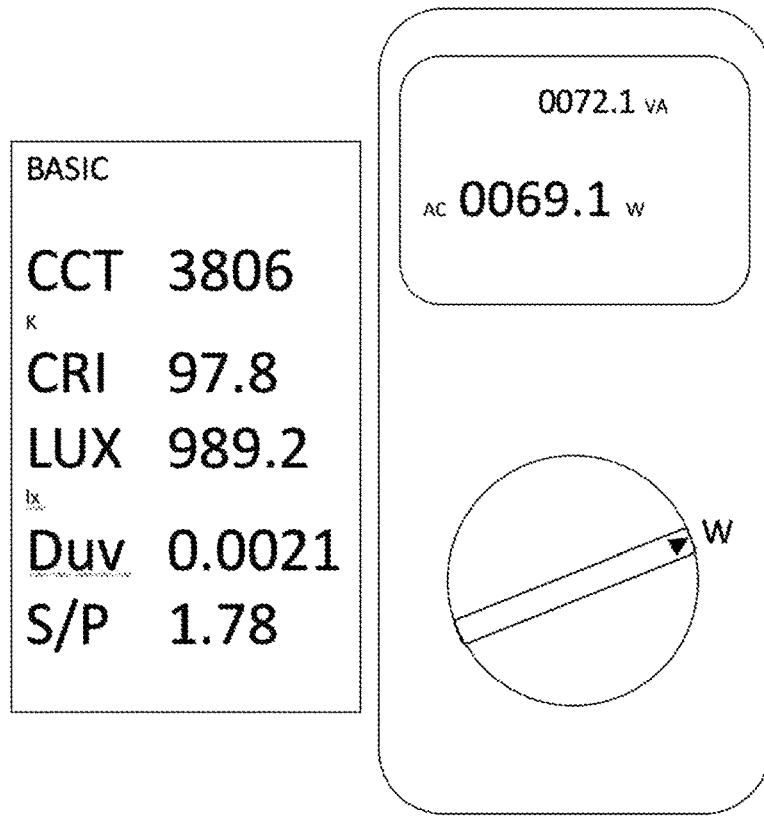
Fig. 4 - Prior Art

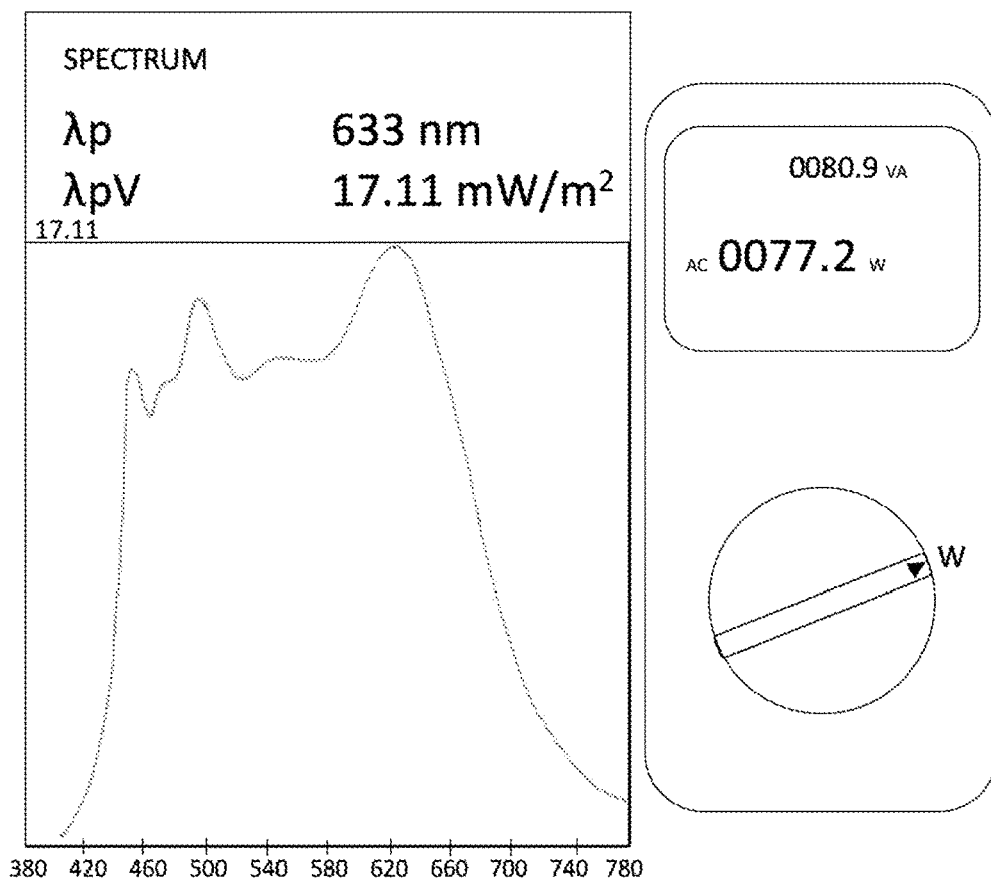
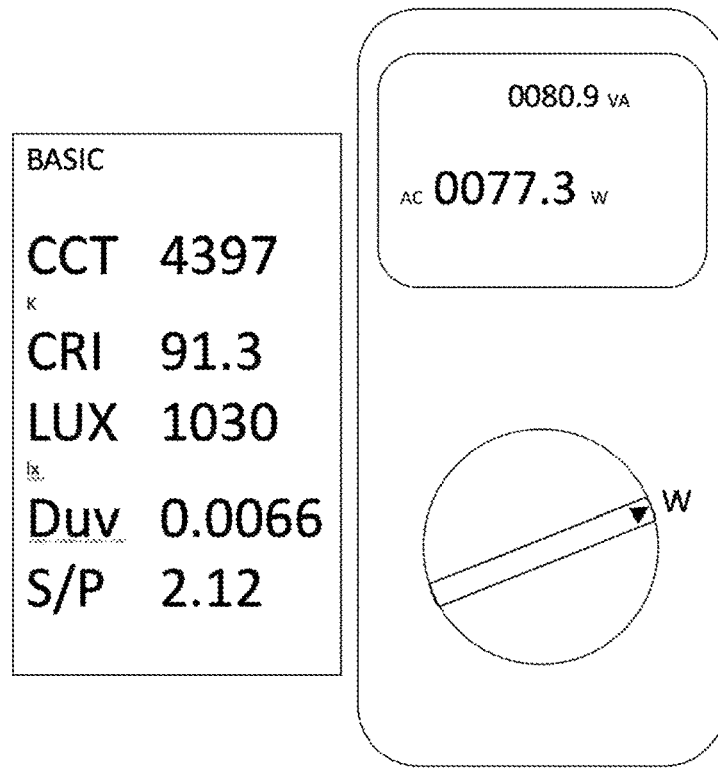
Fig. 9

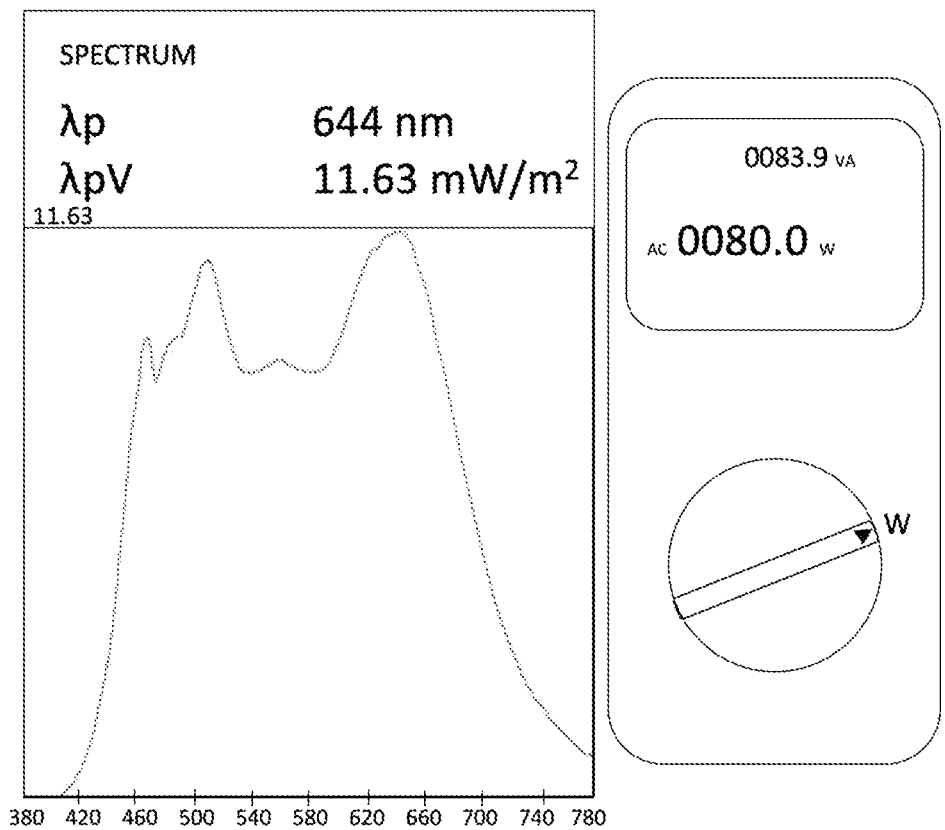
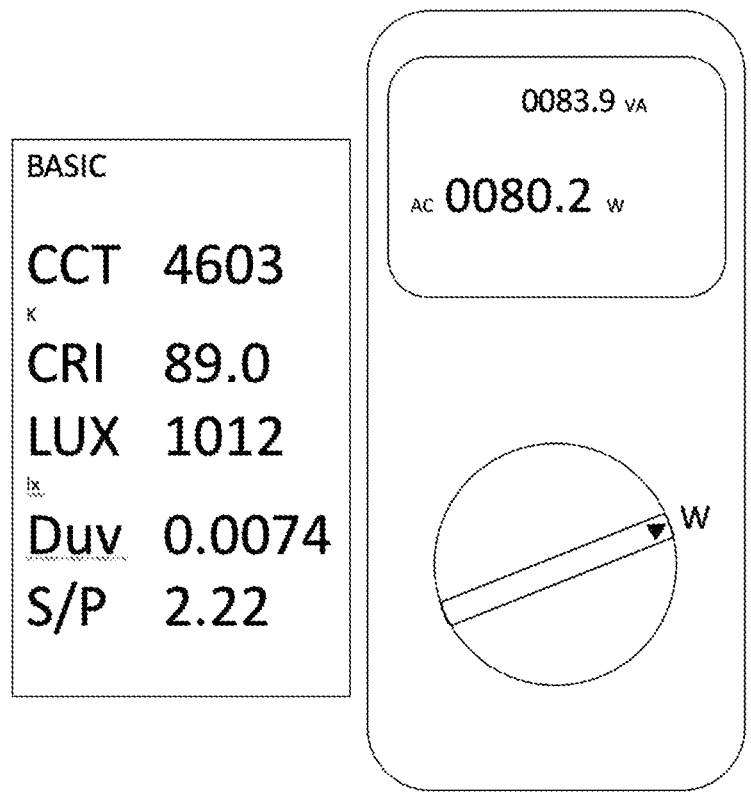
Fig. 11

LED LIGHTING SOURCE FOR IMPROVED COGNITIVE PERFORMANCE AND WITH SUN-LIGHT PROPERTIES

FIELD OF TECHNOLOGY

A light source that rises human cognitive performance and imitates sunlight

STATE OF THE ART

The light is regarded as one among the most important factors with effect on the human circadian system. Developing industry and technologies, the mankind has expanded a day artificially, especially in winter months. We go to sleep late in the evening or work in night shifts when we must be fully watchful. However, most of us, either in a household or in an office, use unsuitable lighting that will not wake us when we need it.

The biological clock, or the central oscillator controlling circadian rhythms situated in suprachiasmatic nuclei (SCN) are effected by the light indirectly through eye retina. Thus the eye, beside vision, also processes information about light. Epiphysis synthetises neurohormone melatonin which functions as a time marker for synchronisation and stabilisation of circadian rhythms and cyclic turn of sleep and wake in a man. Using melatonin receptors, SCNs get feedback information about quantity of melatonin circulating in the organism. It has been shown that various components of light have various effect on us. Blue light with wavelength 460-480 nm has an exciting effect on us, and on the other hand red light with wavelength 610-700 nm has a calming and allay effect on us, it should appear at the night only when we are going to sleep and we do not want be so efficient. The blue light is undoubtedly important but it can disturb circadian rhythms, effect neuroendocrine systems and take part in expansion of civilisation diseases. We can state generally that the higher the correlated colour temperature (CCT) is, the more blue component it contains. It is a fact that if blue light is used, the required effect can be stimulated with much lower light intensity than with white light. A twenty-minute stimulation with clear white light results in activation of the same parts of the brain as the same stimulation with blue light with intensity 100 times lower.

The blue light serves as a modulator of many functions, including attention, excitement, reaction time, work performance and mood. Pro-cognitive effect of light passes through thalamo-cortical projection, brain stem and ascending neurons of the reticular activation system. It was shown that improved attention after evening application of blue light persists even till the next day. Beside attention, the blue light also has effect on more complex cognitive activities. Important effect of blue LED diodes on visual-spaces ability to rotate objects in 3D was shown.

The effect of blue light on cognitive functions was compared with the effect of caffeine. Blue light and caffeine were tested and compared also under a real situation in driving on highway at night. Volunteers got 200 mg of caffeine or had blue light with wavelength of 468 nm switched-on in the dash-board in a route of 400 km. The check was a caffeine-free option of coffee. The both tested groups were more efficient than the group with caffeine-free coffee. (ŠMOTEK, Michal et al. Effect of blue light on circadian system, sleep and cognitive performance. Národnústav duševniho health—National Institute of Mental Health).

Patent document CN 106994209 has described LED lighting for treatment of depression that contains LED chips emitting blue light and LED chips emitting white light, and the number of LED blue chips to the number of white LED chips is 0.03:0.25. There are many manufacturers producing LED lighting. Seoul Semiconductor came with light Sun-Like which emits the light spectrum similar to day-light. Blue wavelengths were removed by adding violet LED chips. Objects lit with this light seem like being lit by day-light sun. A classic LED with luminophore with blue, yellow and red chips added has a marked drop in the turquoise range and in the red range. Thus this light is not suitable for cognitive performance, and moreover it has very bad value of the colour rendering index. The light labelled HUE by Philips has high correlated colour temperature (up to 6000 K) but it has the light spectrum similar to the above light, thus it has a marked drop in the turquoise range, and therefore it is not suitable for excitement of cognitive performance. Further, LEDs consisting of red, green and blue chips, so called RGB LEDs, are combined very frequently. The white light is generated by overlap of all the parts of the visible spectrum, namely of the red, blue and green. A wide range of colour spectrum can be achieved using these combined diodes. The light spectrum generated through colour mixing has, however, a drop in the turquoise to green range and also in the orange range, and thus no excitement of cognitive performance occurs.

DESCRIPTION OF THE INVENTION

A unique source of LED lighting was manufactured that increases the cognitive performance, and it is equal to the sun light with its properties in the biologically beneficial radiation range in 90%. The human cognitive performance is the required property within labour hours and in any activity when we must be alert, or even we need the maximum concentration and the maximum mental performance, for example in studying, solving demanding tasks, extended concentration and the like.

The LED lighting source to improve cognitive performance and with sun-light properties consists of three, at least, types of LED chips: white chips which are blue chips covered with luminophore, monochromatic blue LED chips and turquoise monochromatic LED chips. The spectrum thus composed has a specific spectral composition and it represents the best part of the sun radiation in the biologically beneficial range of 460 to 660 nm. Shorter wavelengths of ultraviolet radiation no longer affect imaging functions and better visibility, but rather dazzle the user and the light is unpleasant, therefore sunglasses are used outdoors in summer frequently and, moreover, electromagnetic radiation in range 380 to 450 nm is labelled as the blue light hazard and human eye has no receptors for it. On the other side of the light spectrum wavelengths 740 nm and over in the infrared range also do not improve the visual fidelity, they heat the interior only, and this is not required and frequently it is undesirable.

This LED light source is marked with distribution of intensity of light power in range 460 nm to 660 nm with up to 25% difference between the maximum and the minimum in the light spectrum in this range. Thus with the minimised drop of light intensity in the spectrum wavelengths.

Such a spectrum is continuous to, at least, 75% of its maximum where the spectral colours of the source with the lowest power that are determined by the minimums of the spectrum reach 75% of radiation intensity and more.

The spectrum of a LED lighting source is close up to 91% to the spectrum radiated by the sun, namely concerning the balance of maxima and minima in distribution of light power depending on wavelength in the biologically beneficial range of 460 nm to 660 nm.

It is advantageous if also a LED chip with radiation in the green-yellow range between 500 to 580 nm, at least, is added to complete the intensity of the yellow-green range in the radiated spectrum, for the sake of the maximum approximation of the sun spectrum. The light spectrum of a LED lighting source with intensity added in the yellow-green range is characterised by distribution of light power in range 460 nm to 660 nm with up to 15% difference between the maximum and minimum in the light spectrum in this range. Thus with the minimised drop of light intensity in the spectrum wavelengths when the light power distributed across the radiation wavelengths differs not more than by 15%.

Thus such a spectrum is continuous to, at least, 85% of its maximum, where the spectral colours of the source with the lowest power that are determined by the minimums of the spectrum reach 85% of radiation intensity and more.

The spectrum of a LED lighting source is close up to 98% to the spectrum radiated by the sun, namely concerning the balance of maxima and minima in distribution of light power depending on wavelength in the biologically beneficial range of 460 nm to 660 nm.

It is advantageous, if the new LED lighting sources with properties of the sun radiation are composed of four light sources with a defined mutual distribution of light power which is given by output and light output of the individual chips. The LED lighting source only operates as a unit. When replacing a single chip type with another, the LED lighting source is misaligned, and it does not show the required compact parameters any more. It is always necessary to keep the basic ratio of light outputs of the light LED sources against a white LED chip with correlated colour temperature 3800 to 4200 K and CRI 90 to 98.

The LED lighting source is set to a white light LED source with correlated colour temperature 3800 to 4200 K, and it is advantageous if 4000 K. In case that a white light source with lower correlated colour temperature, for example 2700 K, is used, which is used as a source of warm white light imitating sunset light, the system will lack light power in the blue range, concerning colour composition the LED lighting source will lose correct neutrality and it will shift into a green tint of irradiated light. On the other hand, if a white light source with higher correlated colour temperature, for example 5500 K, is used, which is used in flash units in making photos, the system will lack light power in the red range, and concerning colour composition the LED lighting source will again lose correct neutrality and it will shift into a blue tint irradiated light.

Any LED chip consists of semiconductor alloys. It is advantageous if a typical semiconductor available for blue LEDs is semiconductor of the multiple quantum well type, namely Indium-Gallium Nitride (InGaN), Zinc Selenide (ZnSe) or Silicon Carbide (SiC) and again it is advantageous, if semiconductor for turquoise LEDs is semiconductor of the multiple quantum well type, namely InGaN only more doped with In, when the light spectrum shifts into the turquoise range. The white LED chip used consisted of a blue LED chip covered with luminophore emitting a band spectrum in wavelengths range 420 to 780 nm.

The source of LED lighting, which beside blue and turquoise LED chips provides also a green-yellow spectral component using PC lime LED chips, not only facilitates cognitive performance of a person but also simulates the light spectrum emitted by the sun with the colour spectral components even more balanced in the required range, thus 460 nm to 660 nm which is the efficient slot in the sun spectrum that makes sense for good vision.

The model of the LED lighting source with properties of the sun radiation contains: white chip—correlated colour temperature 3800-4200 K, CRI 90-98, emitted spectrum with wavelengths 420 to 780 nm, with share 78 to 85% of the total emitted power or 82 to 87% of the total light flux, turquoise monochromatic LED chip with the maximum radiation intensity at 475±5 nm with share 3 to 7% of the total emitted power or 4 to 7% of the total light flux of the source, blue monochromatic LED chip with the maximum radiation intensity at 495±5 nm with share 3 to 7% of the total emitted power and 1 to 4% of the total light flux of the source, because we get to the visible range limit, and visible light is only a part of the total electromagnetic radiation.

It is advantageous if it contains
green-yellow—PC lime LED chip with share 6 to 9% of the total emitted power or 10 to 15% of the total light flux of the source.

The ideal ratio of light output in lm of the light sources—LED chips
white LED:green-yellow PC lime LED:turquoise LED:blue LED amount to 100:9:6:3.

It is advantageous if such lighting is achieved combining a white LED chip, 3800 to 4200 K, CRI 90 to 98 which has a continuous spectrum with characteristic drop in range 460 to 530 nm, which is caused by excitation of a a blue LED chip around 450 nm and by shift of blue light on passing through luminophore into the green-yellow-red range of wavelengths 520 to 740 nm,
a monochromatic blue LED chip, with maximum radiation at 475±5 nm,
a monochromatic turquoise LED chip, with maximum radiation at 495±nm
and it is advantageous if a green-yellow PC lime LED chip, which has a continuous spectrum caused by excitation of the blue LED chip around 420 nm, and by shift of blue light on passing through luminophore into the green-yellow range of wavelengths 500 to 650 nm.

And the essential property is the mutual ratio of light output, or light efficiency of the LED chips and their share on a single lamp to get the balanced light spectrum in range 460 to 660 nm. This means the maximum balance of all the spectral maxima of the source LED chips into the equal intensity.

The LED chips with the following parameters were chosen for presentation:
1. Up to now, the best white LED chip with correlated colour temperature 4000 K and colour rendering fidelity 98, with light output 70 lm/W and power 1.395 W, representing 51.2% of the total radiation output,
2. Blue monochromatic LED chip, with maximum radiation at 475 nm, with light output 29.45 lm/W and power 1.46 W, representing 20% of the total radiation output,
3. Turquoise monochromatic LED chip, with maximum radiation at 495 nm, with light output 64.10 lm/W and power 1.56 W, representing 20% of the total radiation output,
4. Green-yellow PC-lime LED chip, irradiating a continuous spectrum in range 500 to 600 nm, with light output 96 lm/W and power 1.395 W, representing 8.8% of the total radiation output.

A cognitive LED lighting source contains one white LED chip, at least, one blue LED chip, at least, and one turquoise LED chip, at least. It is advantageous if more chips are used according to the size and required output of the LED lighting source. It is advantageous if the chips are fitted on a printed circuit which forms a section, it is advantageous, if the construction length of the printed circuit section is 5 to 8 cm. The printed circuit sections are joined by soldering, after edges overlapped. The joined printed circuits form a light strip with variable length. Each section contains several LED chips put in series, the sections are put in parallel in the strip.

The cognitive source contains LED chips with precisely balanced ratio of output of white LED chips to blue and turquoise LED chips, it is advantageous if the ratio among white LED chips:blue LED chips:turquoise LED chips amount to 1:0.03 to 0.05:0.03 to 0.05. The cognitive LED lighting source has selectable ratio of output of the LED chips where LED chips with lower output are fitted in a higher share to balance their lower radiation intensity to provide for necessary output of those LED chips.

It is surprising that this unique established ratio for the LED lighting source for cognitive output provides for completion of the full irradiated spectrum of the cognitive LED lighting source up to the level of both light maxima of the white LED chip in the range of the blue-to-green transition, thus wavelengths in the blue and turquoise ranges. This way the light emitted spectrum becomes continuous to, at least, 75% of light intensity. This specific addition of the blue and turquoise monochromatic LED chips will cause/provide for large approximation of irradiated light to sun radiation where the intensity of light radiation in the range of the blue-to-green transition and in the spectral range of light 460 to 660 nm is almost balanced to 80% of intensity of light radiation irradiated by the sun, as shown in FIG. 1.

The whole system of the cognitive LED lighting source is set in such a way that 4.5 to 6% of blue and turquoise light radiation is added to the light radiation from the white LED chips and it is advantageous if of equal radiation intensity. This provides for balancing the radiation intensity in range of the blue-to-green transition against the red range almost to the sunshine level. The generated combined light radiation of the cognitive LED lighting source has CRI 98 and correlated colour temperature 4000 to 4700 K, sun radiation has correlated colour temperature 4982 K and CRI 99.5.

It is advantageous, if the light source for cognitive performance uses two, at least, light strips. A white strip which is fitted with white LED chips only. A blue strip which contains monochromatic blue LED chips with monochromatic turquoise LED chips with equal output and it is advantageous if output of one white LED chip is 0.17 W. It is advantageous if monochromatic blue LED chips alternate with monochromatic turquoise LED chips with equal output in the other light strip, and it is advantageous, if blue and turquoise LED chips are in share 1:1. It is advantageous if light output of one blue or turquoise chip is 0.09 W.

The length of the light strip and number of LED chips can vary but the ratio of light output of white LED chips: (Blue+turquoise) 1:0.03 to 0.05 must be adhered to. It is advantageous if the light output of blue and turquoise LED chips amounts to 4.5 to 6% of light output of white LED chips, respectively input of blue and turquoise LED chips amounts to 13 to 15% of white LED chips input. It was established that white LED chips themselves had input 85 to 87% of the total input and after the blue-turquoise strip was switched on, the input increased by 13 to 15%.

It is advantageous if the cognitive LED lighting source contains two, at least, light strips, consisting of a printed circuit fitted with white, blue and turquoise chips, connected to a voltage multiplier which in turn is connected to a current supply. It is advantageous if a dimmer is connected behind the voltage multiplier to regulate input current used to cut down intensity of radiation of the light strips.

It is advantageous if the LED lighting source which contains also green-yellow PC lime LED chips contains LED chips connected in two channels, and the I channel contains 20 to 80 white LED chips and the II channel contains one to eight groups of blue-turquoise-green-yellow LED chips, and one group of LED chips contains one blue LED chip, one turquoise LED chip and one green-yellow PC lime LED chip. It is advantageous if the group of blue-turquoise-green-yellow LED chips also contains one to 4 white LED chips.

It is advantageous if the I channel contains 40 to 60 white LED chips and the II channel contains four groups of blue-turquoise-green LED chips.

It is advantageous if the I channel contains 48 white LED chips and the II channel contains four groups of blue-turquoise-green-yellow LED chips and four white LED chips.

It is advantageous if the LED lighting source which also contains green-yellow PC lime LED chips consists of three lines of chips and it is advantageous, if the first and the third lines contain white LED chips from the I channel only and the second line contains chips from the II channel, thus groups of blue-turquoise-green-yellow LED chips alternating with a white LED chip.

BRIEF DESCRIPTION OF THE DRAWINGS

FIG. 2: Light spectrum of classic LED with correlated colour temperature 4000 K with CRI 80.
FIG. 3: Light spectrum of white LED chip with correlated colour temperature 3957 K and CRI 98
FIG. 4: Light spectrum of strip with white LED chips and correlated colour temperature 3806 K and CRI 97.8
FIG. 9: Spectrofotometric spectrum emitted by cognitive LED lighting source according to Example 2.

EXAMPLES OF INVENTION EXECUTION

Figure 1:
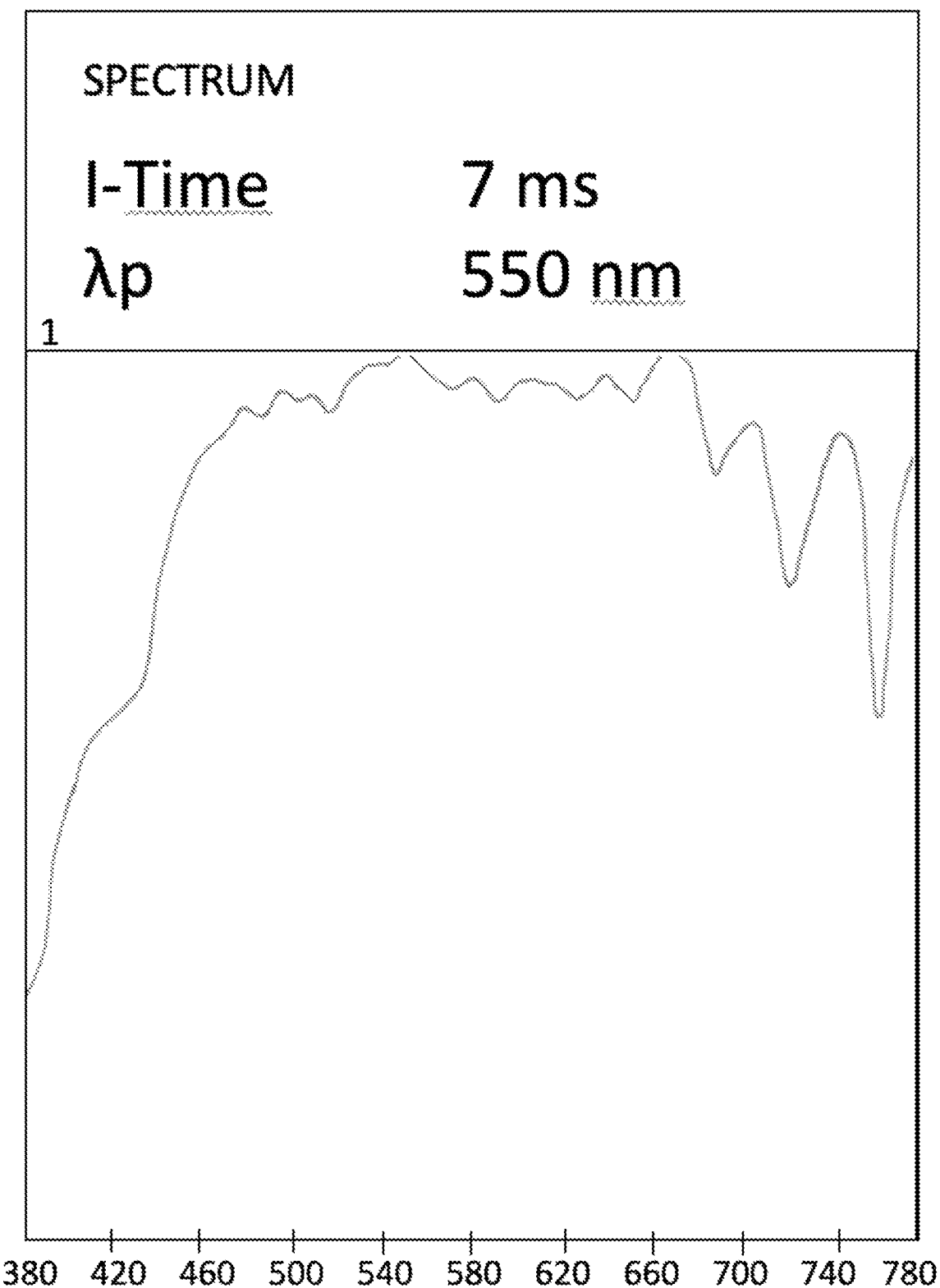
FIG. 1: Light spectrum of day sunlight
Figure 5:
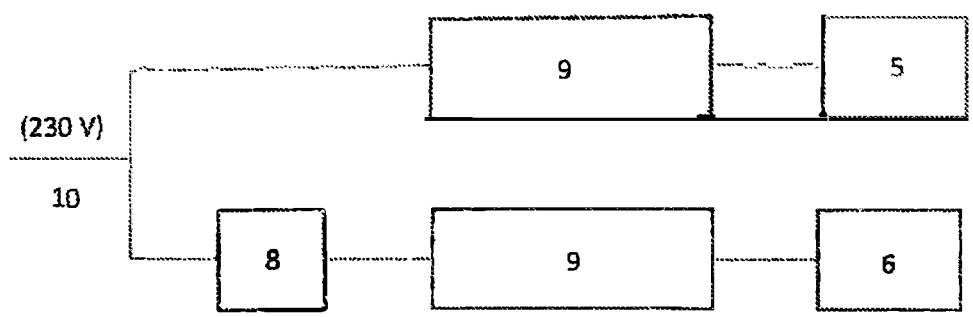
FIG. 5: Scheme of electric connection of light source to improve cognitive performance
Figure 6:
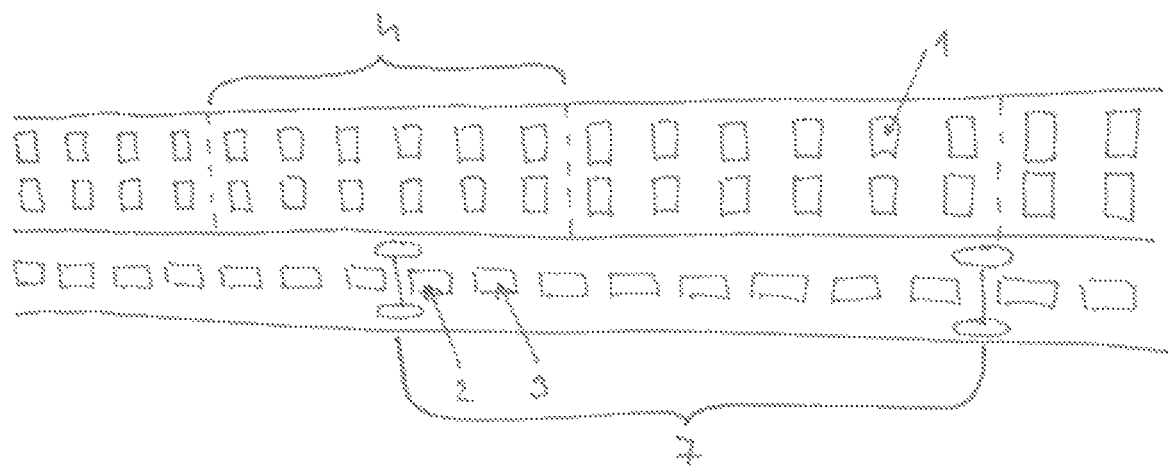
FIG. 6: Figure with printed circuit with LED chips according to Example 1
Figure 7:
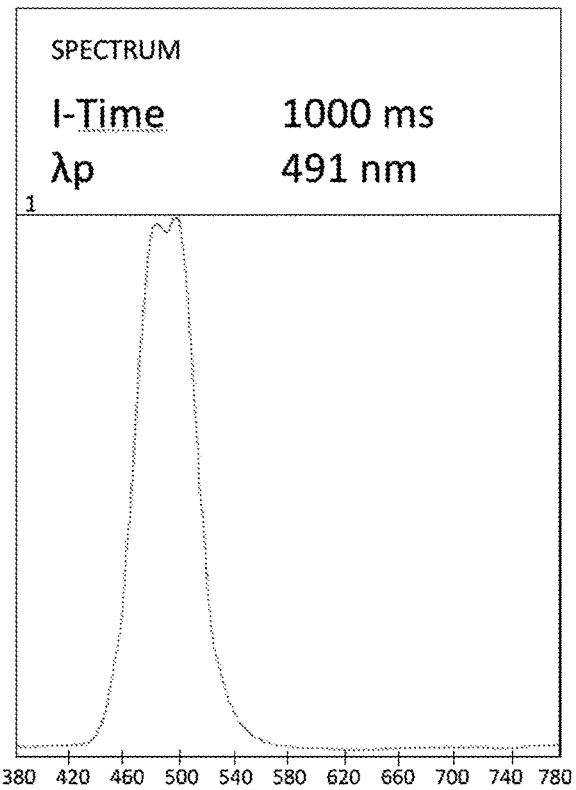
FIG. 7: Light spectrum of light strip with monochromatic blue and turquoise LED chips

Example 1—Two Light Strips, Blue and Turquoise LED Chips with Equal Light Output The white LED chip consisted of a blue LED chip with semiconductor InGaN covered with luminophore. It was advantageous if used luminophores were with commercial name ZYP630G3, emitting light with maximum at wavelength of 628 nm and ZYP555G3, emitting light with maximum at wavelength of 555 nm which were dispersed in a silicone case that was applied over the blue LED diode. The case of the LED diode can have various shape, and it is advantageous if the slope of a wall of the case of the LED diode is inclined by 20° against level.

A cognitive LED lighting was created with two 1 m long light strips 5 and 6 which consisted of printed circuits fitted with LED chips, and the strips were connected to voltage multipliers 9 which were connected to current source 10. White light strip 5 was fitted with 240 white LED chips 1 which were positioned in two lines and one printed circuit 4 with length of 5 cm was fitted with 12 white LED chips 1. White LED chip 1 consisted of a blue LED chip of InGaN semiconductor, covered with luminophore with marks ZYP555G3 and ZYP63063 in ratio 1:2. The light emitted from the white LED chip 1 formed a continuous band spectrum at wavelength 380 to 700 nm with correlated colour temperature 3957 K and CRI 98. White light strip 5 with white LED chips 1 had light output 41 W/m. Light strip for blue and turquoise chips 6 with length of 1 m was fitted with 55 monochromatic blue LED chips 2 of InGaN semiconductor with maximum radiation at 475 nm and 55 monochromatic turquoise LED chips 3 of InGaN semiconductor with maximum radiation at 495 nm. One printed circuit 4 with length of 7.2 cm was fitted with four blue LED chips 2 and four turquoise LED chips 3 which alternated. Light strip for blue and turquoise chips 6 had output 3 W/m. The ratio of luminosity of LED chips white:blue:turquoise was 1:0.3:0.3. The share of chips was 4:1:1.

Figure 10:
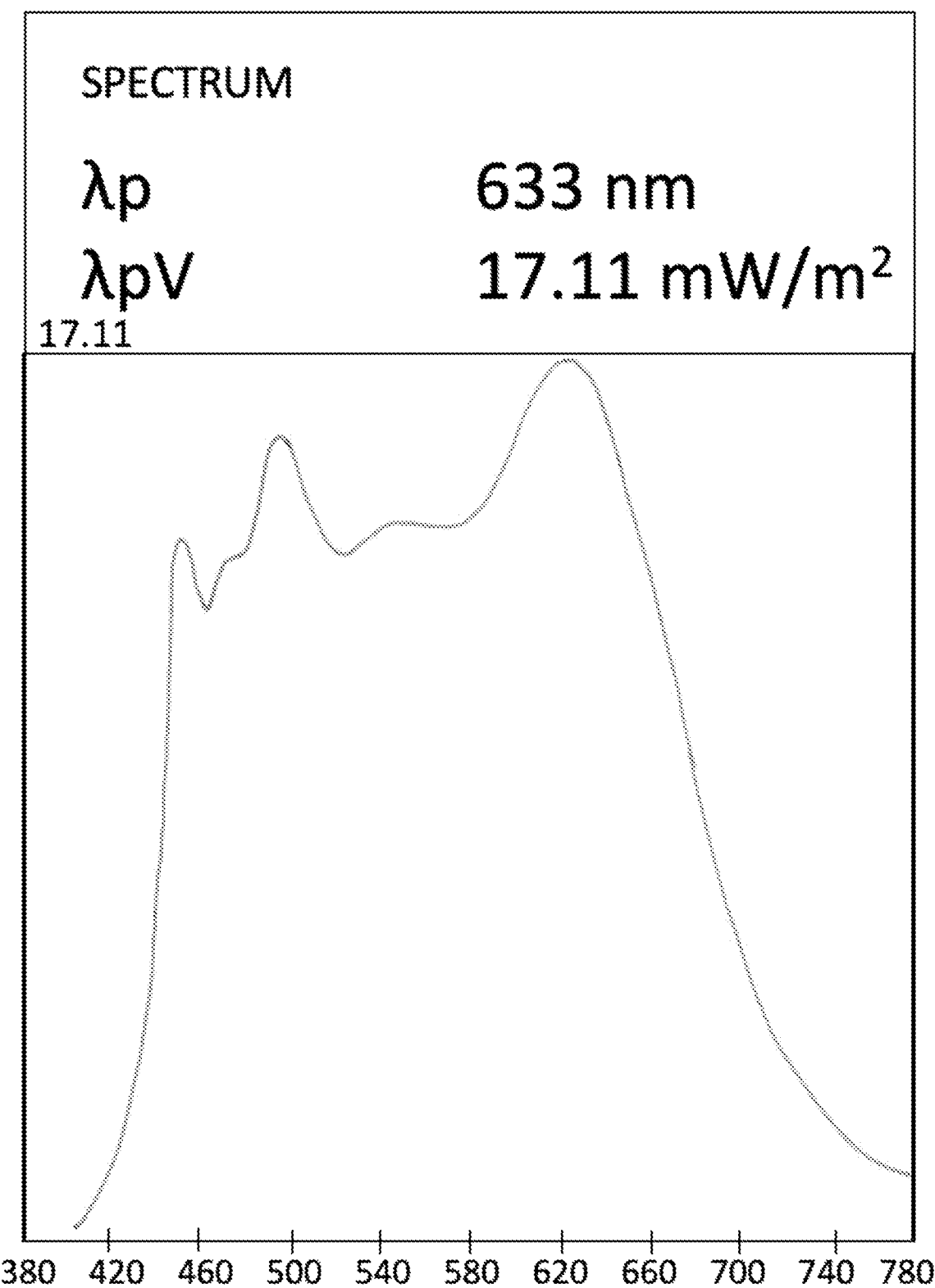
FIG. 10: Detail of spectrum in FIG. 9
FIG. 11: Spectrofotometric spectrum emitted by cognitive LED lighting source according to Example 1.
Figure 12:
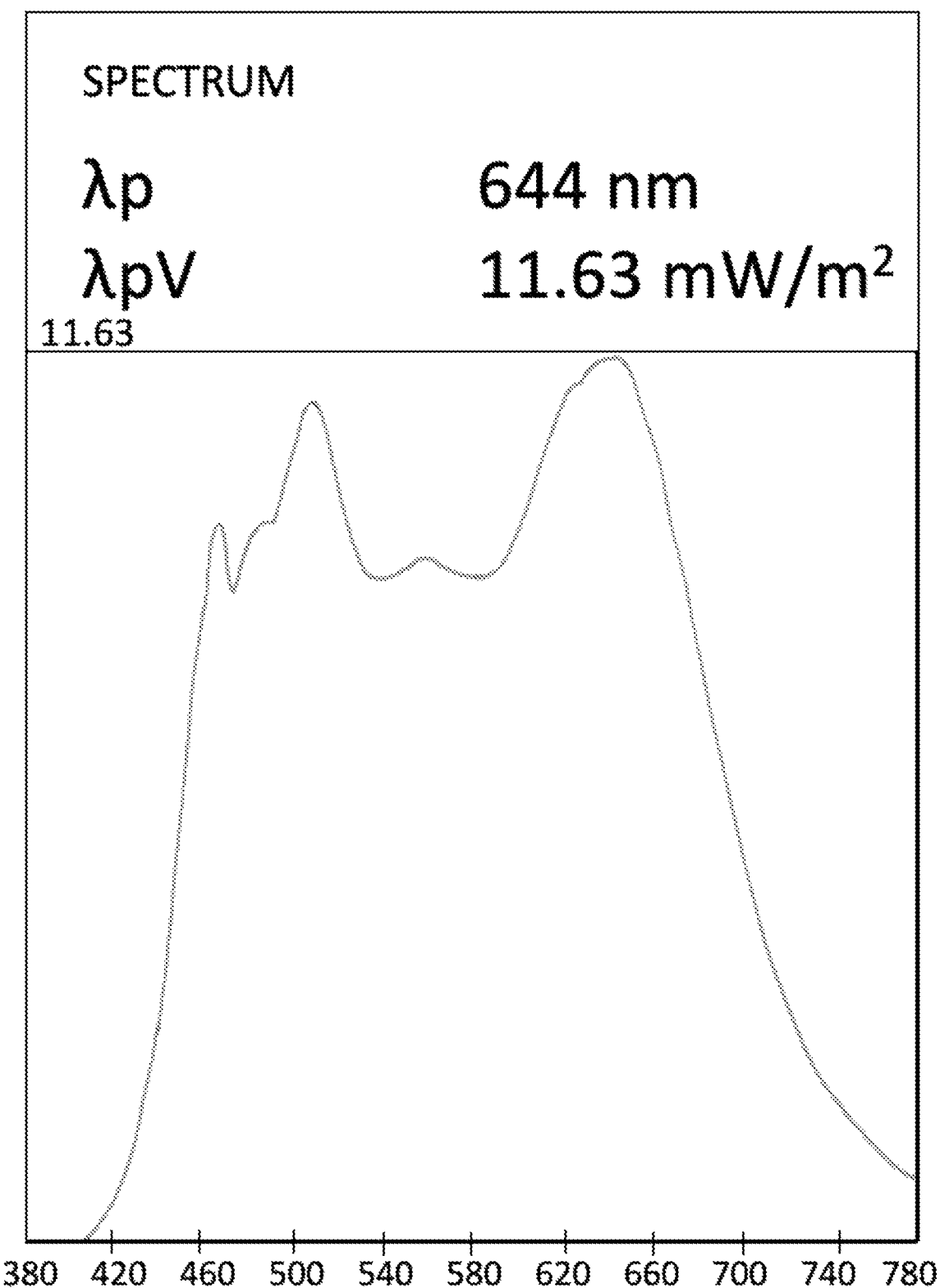
FIG. 12: Detail of spectrum in FIG. 11.
Figure 13:
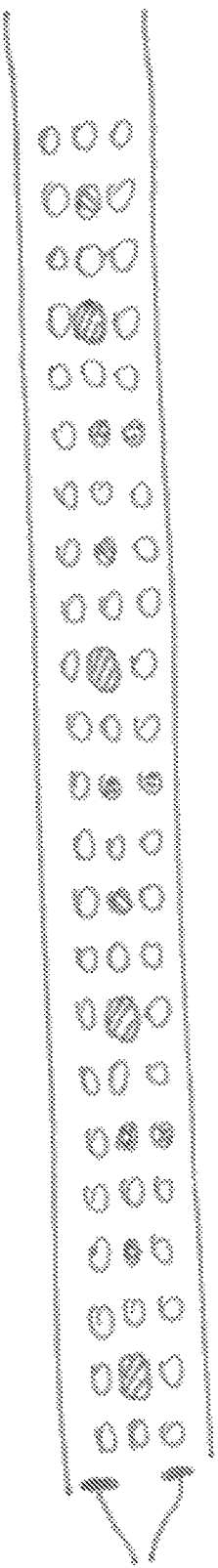
FIG. 13: Light strip equipped with LED chips in two channels according to Example 5
Figure 14:
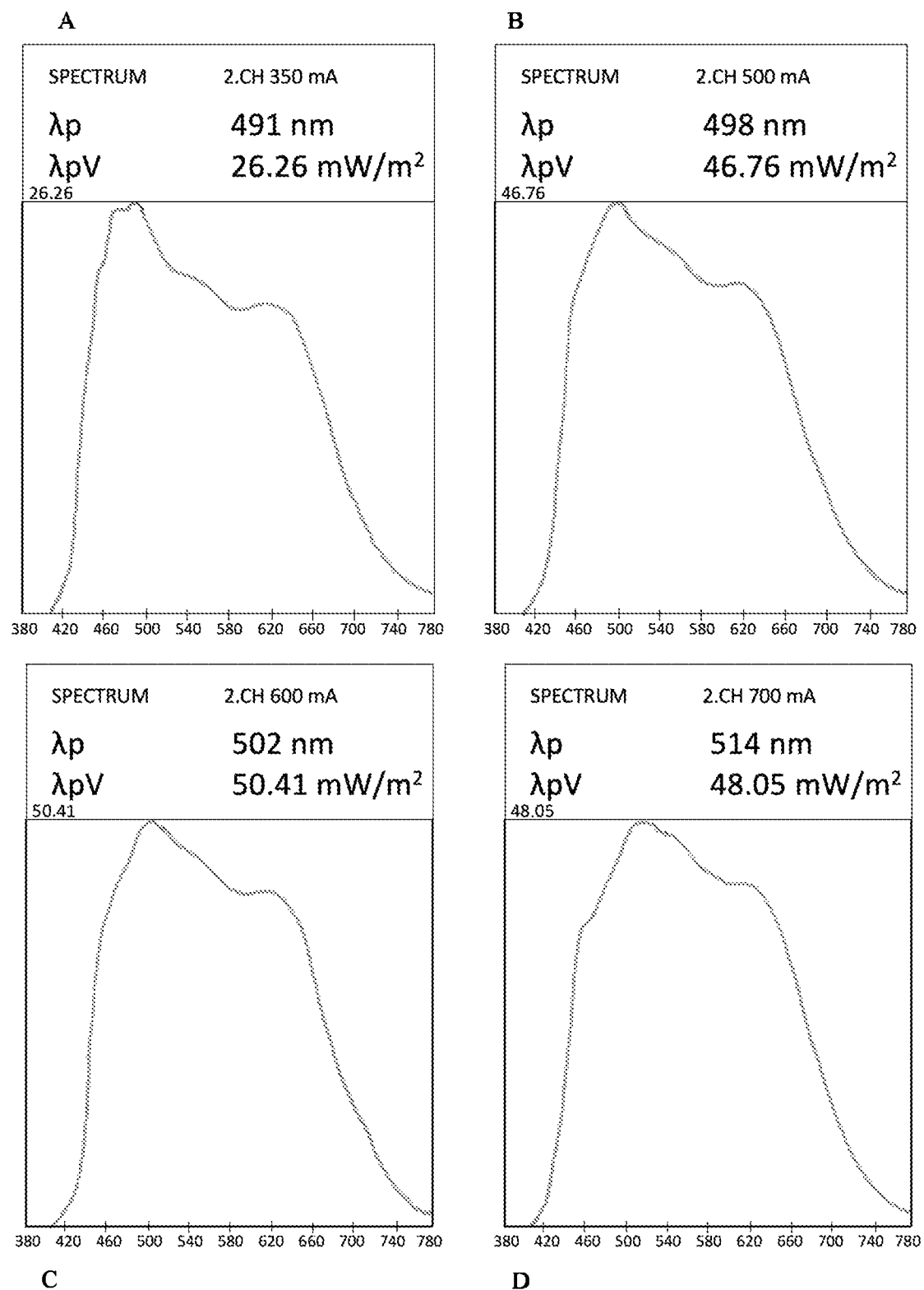
FIG. 14: 14A: Light spectrum emitted by strip according to Example 5 when only II channel was on and current was 350 mA, 14B: Light spectrum emitted by strip according to Example 5 when only II channel was on and current was 500 mA, 14C: Light spectrum emitted by strip according to Example 5 when only II channel was on and current was 600 mA, 14 D: Light spectrum emitted by strip according to Example 5 when only II channel was on and current was 700 mA.
Figure 15:
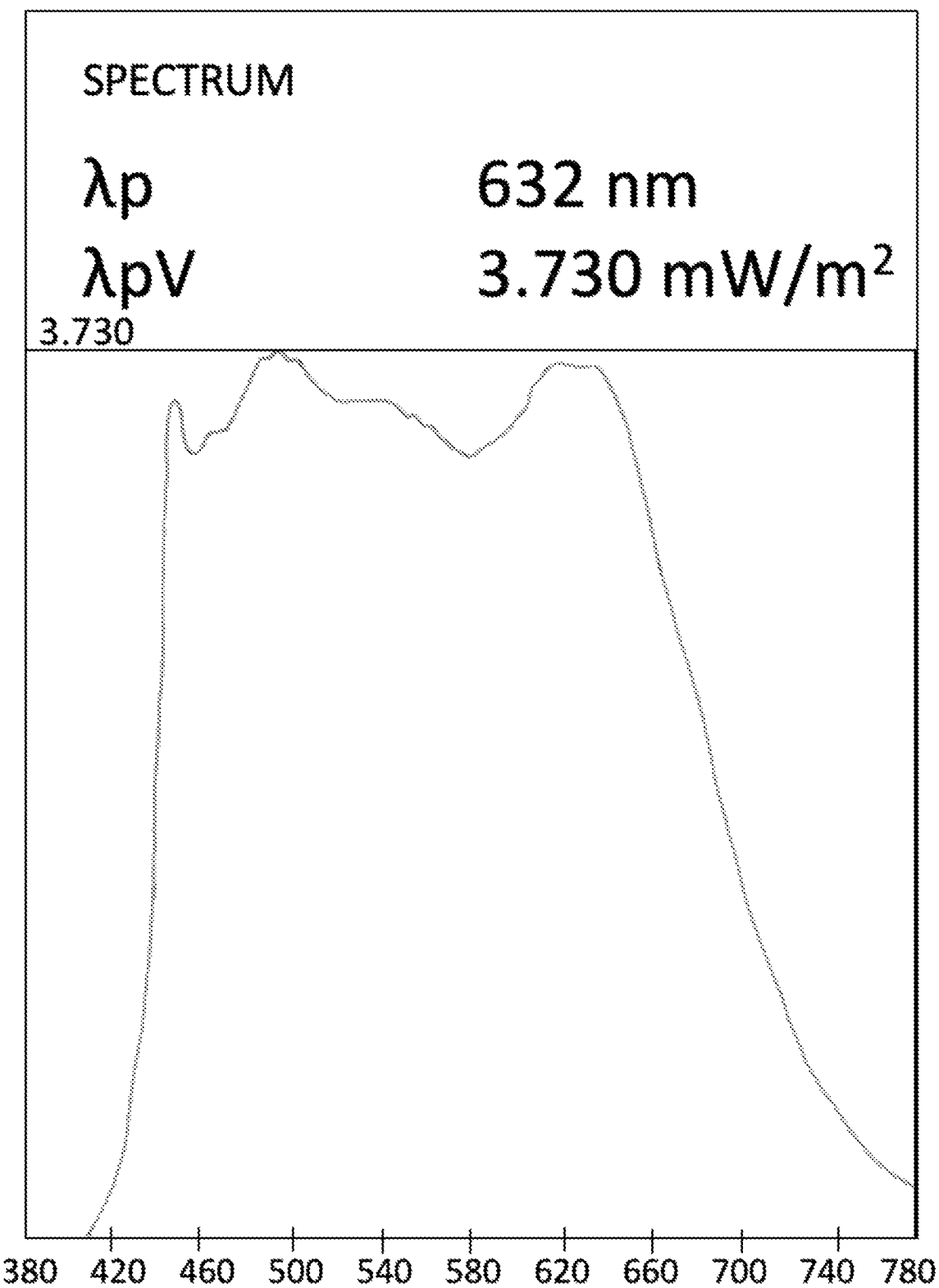
FIG. 15: Spectrum emitted by LED lighting source according to Example 5
Figure 16:
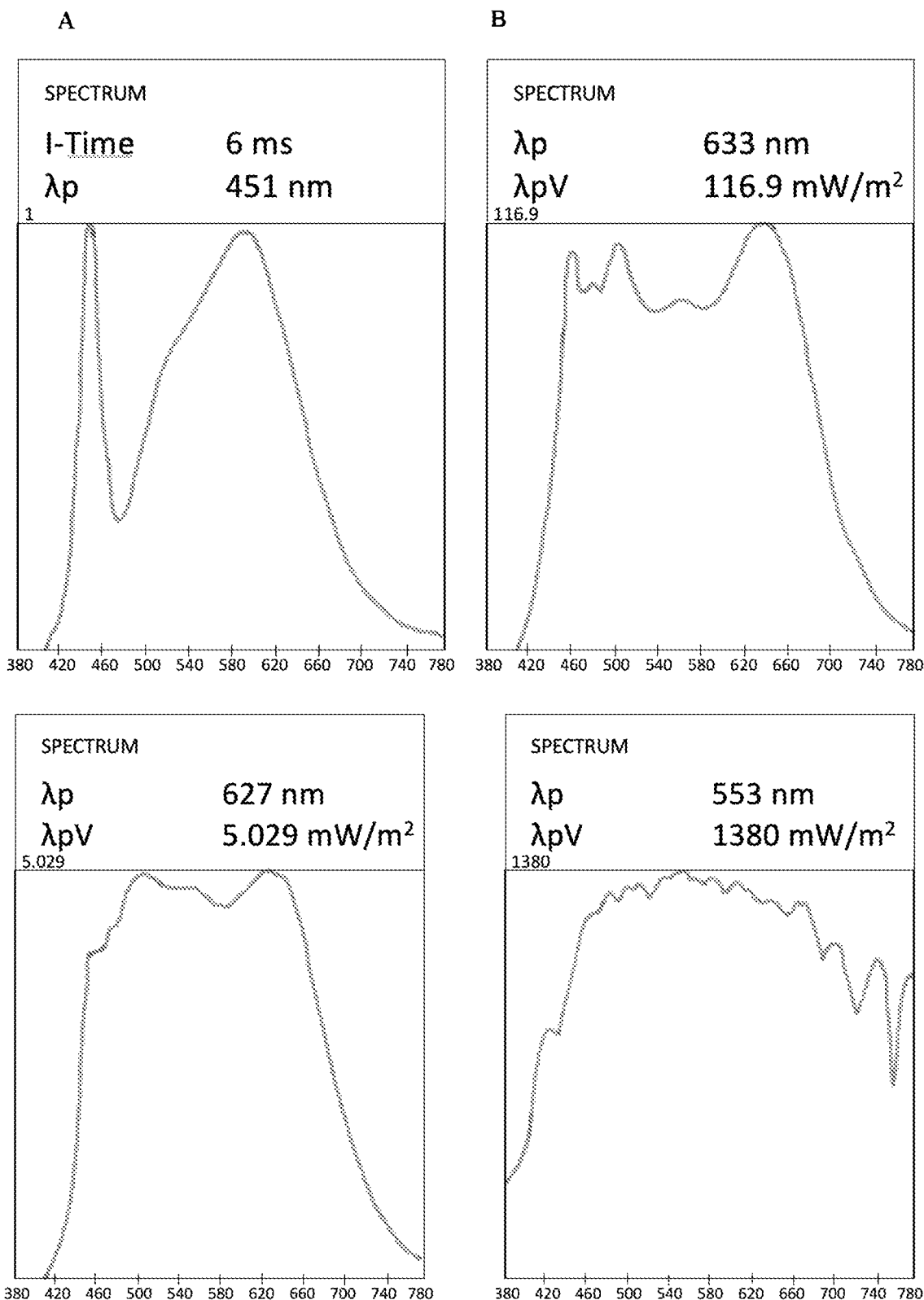
FIG. 16: 16A: Comparison of spectra of light sources: Spectrum of white LED chip with correlated colour temperature 4000 K and CRI 90 16B: Comparison of spectra of light sources: Spectrum emitted by LED lighting source according to Example 1, cognitive light source 16C: Comparison of spectra of light sources: Spectrum emitted by LED lighting source according to Example 5, with properties of sun radiation 16D: Comparison of spectra of light sources: Spectrum of day sunlight
Figure 17:
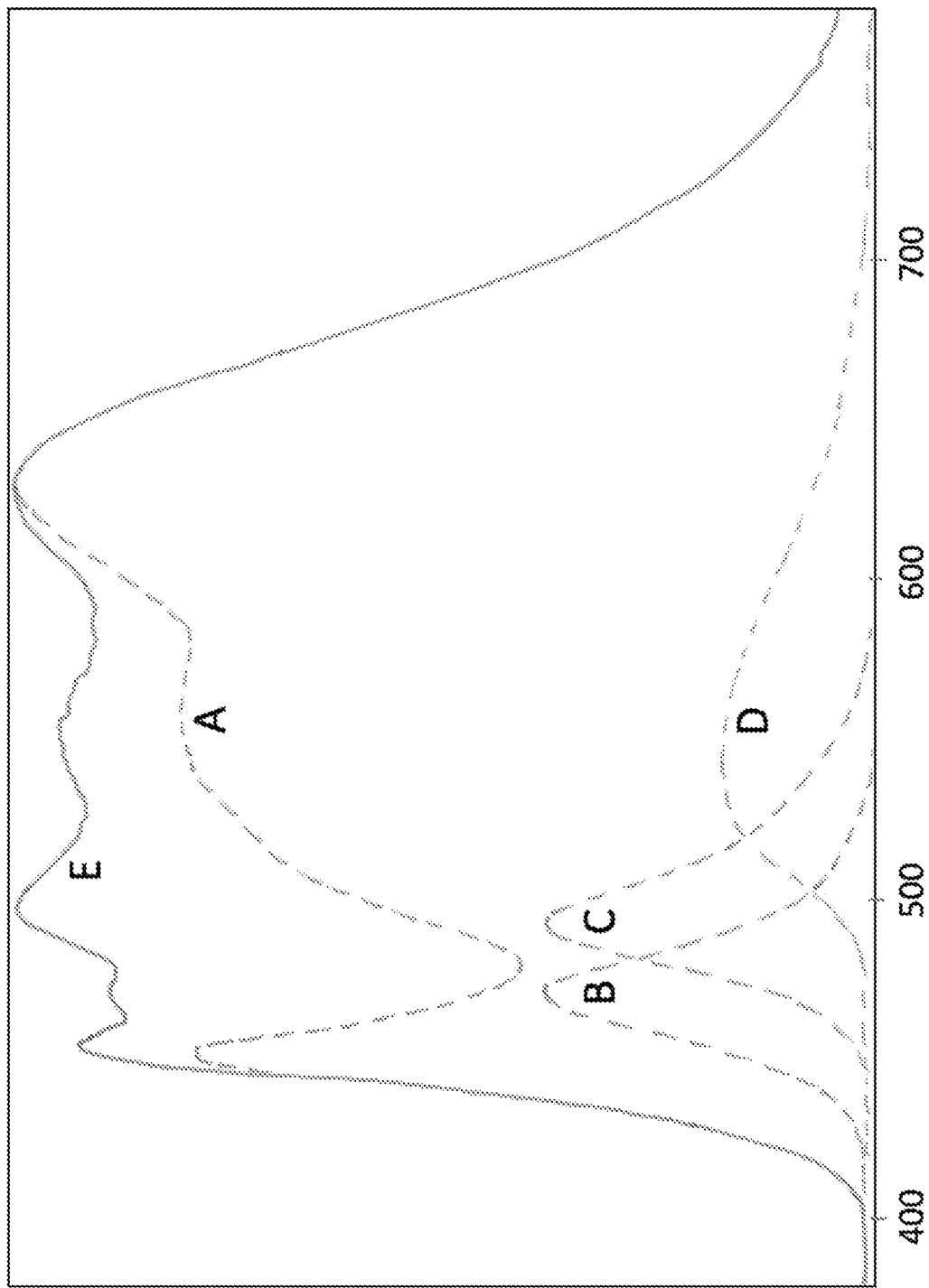
FIG. 17: Graph of spectra of all light sources of used LED chips, A-white LED chip 4000 K, B-blue LED chip, C-turquoise LED chip, D-PC lime LED chip, E-LED lighting source with properties of sun radiation according to Example 5
Figure 18:
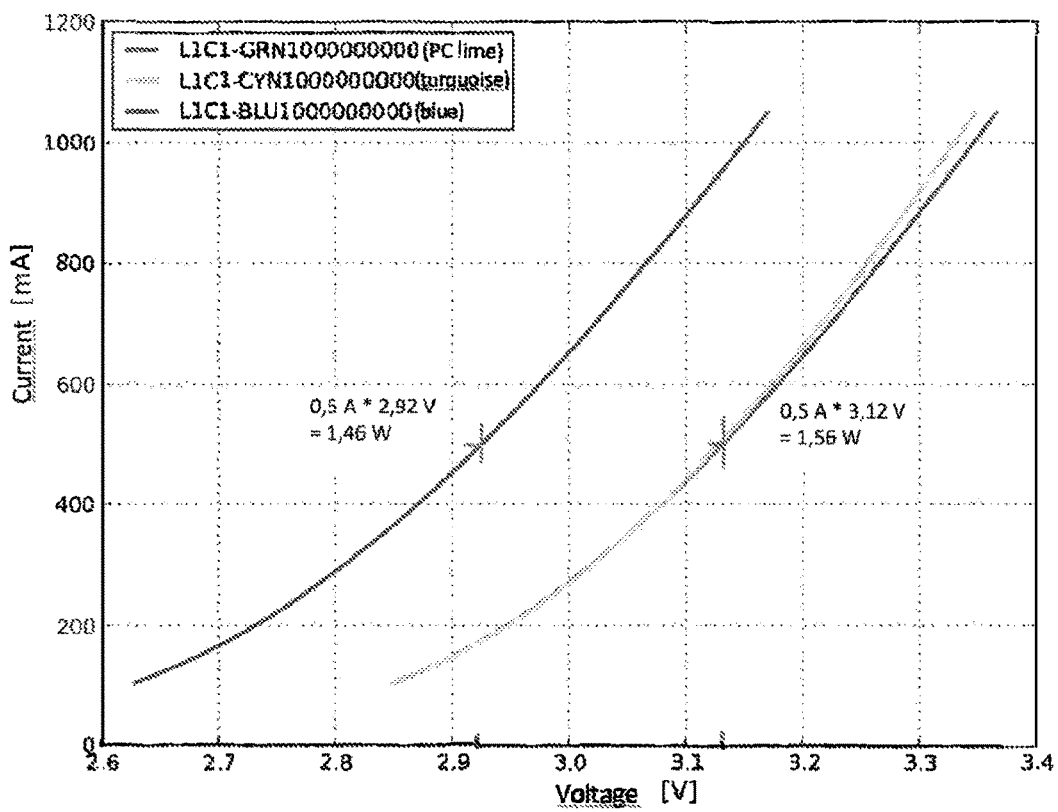
FIG. 18: Voltage responses of LED chips as depending on transient current

Characteristic parameters were measured with a manual spectrometer UPRtek for this source, emitted light had CRI 89 with correlated colour temperature 4603 and the spectrum of irradiated light was in range 420 to 760 nm, rated field of radiation from range 460 to 650 nm generated 80% of light intensity of sun radiation, as shown in FIG. 10.

Reception of cognitive LED lighting was also measured, it was 80.2 W.

Example 2—Two Light Strips, Blue and Turquoise LED Chips with Different Light Output A cognitive LED lighting was created with two 1 m long light strips, a light strip of white chips 5 and a light strip of blue and turquoise chips 6 which consisted of printed circuits fitted with LED chips, and the strips were connected to voltage multipliers 9 which were connected to current source 10. The light strip of white chips 5 was fitted with 240 white LED chips 1 in two lines, and the one printed circuit 4 with length of 5 cm was fitted with 12 white LED chips 1. White LED chip 1 consisted of a blue LED chip of ZnS semiconductor, covered with luminophore with mark ZYP555G3 and ZYP63063 in ratio 1:2. The resulting light emitted from the white LED chip 1 formed a continuous band spectrum with wavelengths 380 to 700 nm with correlated colour temperature 4000 K. One white LED chip 1 had output 0.17 W, this means that the whole one-meter long white strip had output 41 W/m.

The light strip with blue and turquoise chips 6 with length of 1 m was fitted with 110 monochromatic blue LED chips 2 of InGaN semiconductor with maximum radiation at 475 nm with light output 4 mW and 55 monochromatic turquoise LED chips 3 of semiconductor with maximum radiation at 495 nm with light output 7 mW, this means that the whole one-meter long light strip of blue and turquoise chips 6 had output 825 mW/m. One printed circuit 4 with length of 7.2 cm was fitted with six blue LED chips 2 and two turquoise LED chips 3. Coloured LED chips alternated always as 2 blue and 1 turquoise chips. Characteristic parameters were measured with a manual spectrometer UPRtek for this source, emitted light had CRI 91.3 with correlated colour temperature 4397, and the spectrum of irradiated light was in range 420 to 760 nm, rated field of radiation from range 460 to 650 nm generated 78% of light intensity of sun radiation, as shown in FIG. 10.

Reception of cognitive LED lighting was also measured, it was 77.2 W.

Example 3—Three Light Strips, Blue and Turquoise LED Chips with Different Light Output Three one meter long light strips were created, a light strip with white chips 5, a light strip for blue chips and a light strip for turquoise chips, and LED chips were fitted in them. The light strip of white chips 5 was fitted with 240 white LED chips 1 and printed circuit 4 with length of 5 cm was fitted with 12 white LED chips 1, positioned one after another. White LED chip 1 consisted of a blue LED chip of ZnS semiconductor, covered with luminophore with marks ZYP555G3 and ZYP63063 in ratio 1:2. The resulting light emitted from the white LED chip 1 had correlated colour temperature 4000 K, and light wavelength was 380 to 700 nm. One white LED chip had output 0.17 W, this means that the whole one-meter long white strip had output 41 W/m.

The light strip for blue chips with length of 1 m was fitted with 219 monochromatic blue LED chips 2 of InGaN semiconductor with maximum radiation at 475 nm with total light output 1.5 W/m, output of one chip was 7 mW. The light strip for turquoise LED chips with length of 1 m was fitted with 110 monochromatic turquoise LED chips 3 of InGaN semiconductor with maximum radiation at 495 nm and the total light output 1.4 W/m, output of one chip was 12 mW. Characteristic parameters were measured with a manual spectrometer UPRtek for this source, emitted light had CRI 90 with correlated colour temperature 4650 and the spectrum of irradiated light was in range 420 to 760 nm, rated field of radiation from range 460 to 650 nm generated 80% of light intensity of sun radiation.

Reception of cognitive LED lighting was also measured, it was 80 W.

Example 4—Three Chips

Figure 8:
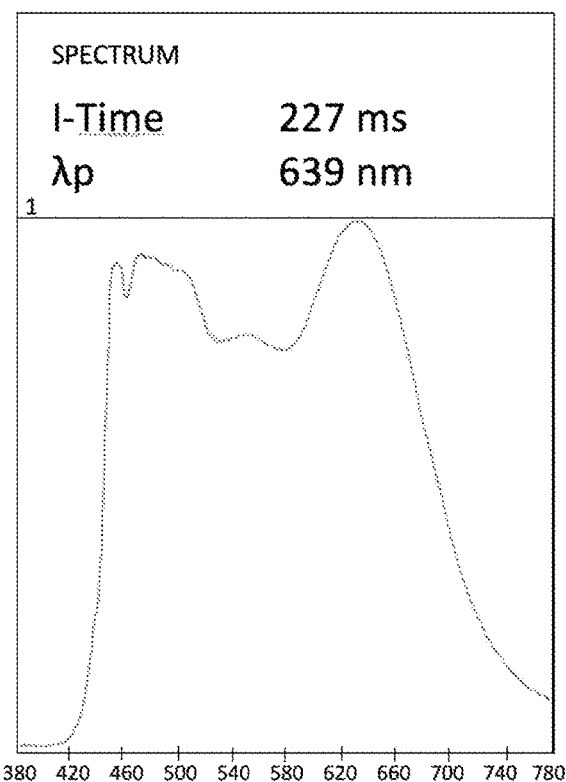
FIG. 8: Spectrofotometric spectrum emitted by cognitive LED lighting source according to Example 4.

A round light source was fitted with three LED chips, one white LED chip with output 2 W with correlated colour temperature 3957 K and CRI 98 of a continuous band spectrum of visible light at wavelength 440 nm to 700 nm, one blue LED chip with output of 60 mW and a turquoise LED chip with output of 60 mW. The white LED chip emitted a continuous band spectrum of visible light at wavelength 440 nm to 700 nm and correlated colour temperature CCT 3800 to 4200 K, and CRI 98. The blue LED chip was of InGaN with maximum radiation at 475 nm and the turquoise LED chip was of InGaN with maximum radiation at 495 nm. Characteristic parameters were measured with a manual spectrometer UPRtek for this source, emitted light had CRI 89.5 with correlated colour temperature 4810 and the spectrum of irradiated light was in range 420 to 760 nm, rated field of radiation from range 460 to 650 nm generated 81% of light intensity of sun radiation, as shown in FIG. 8.

Example 5

A LED lighting source was created that contained one light strip with three lines, and the first and the third lines were fitted with 24 white LED chips, thus 48 white LED chips in total, and connected to the I channel in parallel with 12 chips connected in series, with correlated colour temperature 4000 K and CRI 98, and the middle line was fitted with 4 blue monochromatic LED chips with radiation maximum at 473 to 475 nm, 4 turquoise monochromatic LED chips with radiation maximum at 495 nm, 4 PC Lime LED chips with radiation maximum at 520 nm emitted at 420 nm and 12 white LED chips and connected to the II channel in parallel with 12 chips connected in series, and the middle line consisted of white LED chips alternated with blue, turquoise and PC lime LED chips, this means white, blue, white, turquoise, white, PC lime, white, blue etc.

Properties of the chips were as follows:
white LED chip
output: 0.31 W per one chip in I channel containing 48 chips units, 15.1 W in total, and 0.93 W per one chip in II channel containing 12 chips, 11.1 W in total and total output of white chips: 26.2 W
light efficiency: 70 lm/W
share in total light power: 51.2%
blue monochromatic LED chip with radiation maximum at 475 nm
output: 0.35 W per one chip in II channel containing 4 chips units, 1.4 W in total
light efficiency: 29.45 lm/W
share in total light power: 20%
turquoise monochromatic LED chip with radiation maximum at 495 nm
output: 0.38 W per one chip in II channel containing 4 chips units, 1.5 W in total
light efficiency: 64.1 lm/W
share in total light power: 20%
PC Lime LED chips with radiation maximum at 520 nm
output: 0.78 W per one chip in II channel containing 4 chips units, 3.1 W in total
light efficiency: 96 lm/W
share in total light power: 8.8%

The total output of the source amounts to 32.2 W, 72 units of LED chips

Example 6

A LED lighting source was created that contained one light strip with three lines and the first and the third lines were fitted with 24 white LED chips, thus 48 white LED chips in total, and it was connected to the I channel in parallel with 12 chips connected in series, with correlated colour temperature 2700 K and CRI 98 and the middle line was fitted with 4 blue monochromatic LED chips with radiation maximum at 473 to 475 nm, 4 turquoise monochromatic LED chips with radiation maximum at 495 nm, 4 PC Lime LED chips with radiation maximum at 520 nm emitted at 420 nm, and 12 white LED chips with correlated colour temperature 2700 K and CRI 98, and connected to the II channel in parallel with 12 chips connected in series, and the middle line consisted of white LED chips alternating with blue, turquoise and PC lime LED chips, this means white, blue, white, turquoise, white, PC lime, white, blue etc. The spectrum of this source was measured and found unsuitable for use as a LED lighting source with properties of the sun radiation due to low radiation intensity in the blue range and imbalance of the spectrum in the required biologically beneficial range 460 to 660 nm.

Example 7

Figure 20:
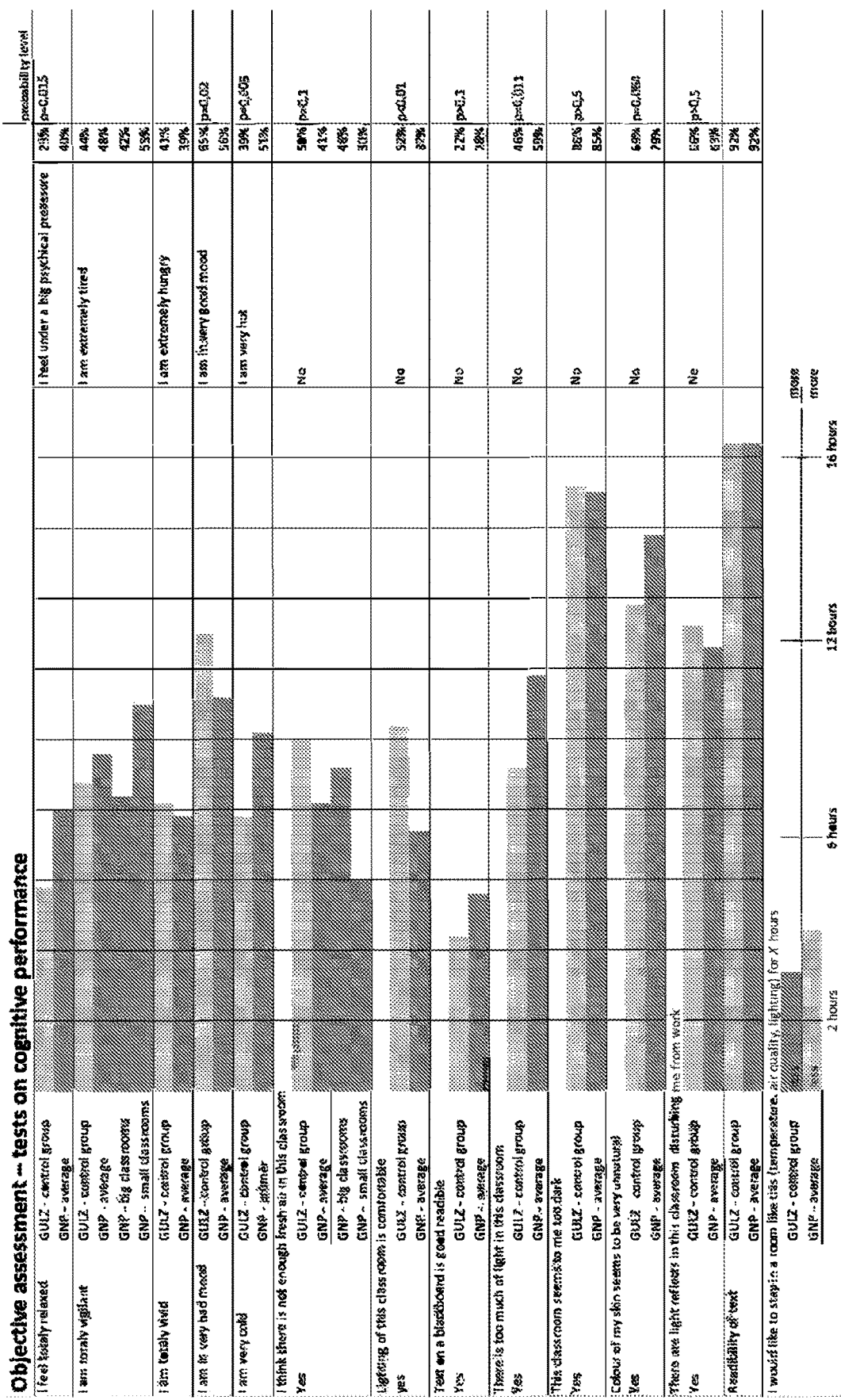
FIG. 20: Averages of subjective assessment of tested (GNP, n=51) and reference (GULZ, n=53) groups according to Example 7.
Figure 21:
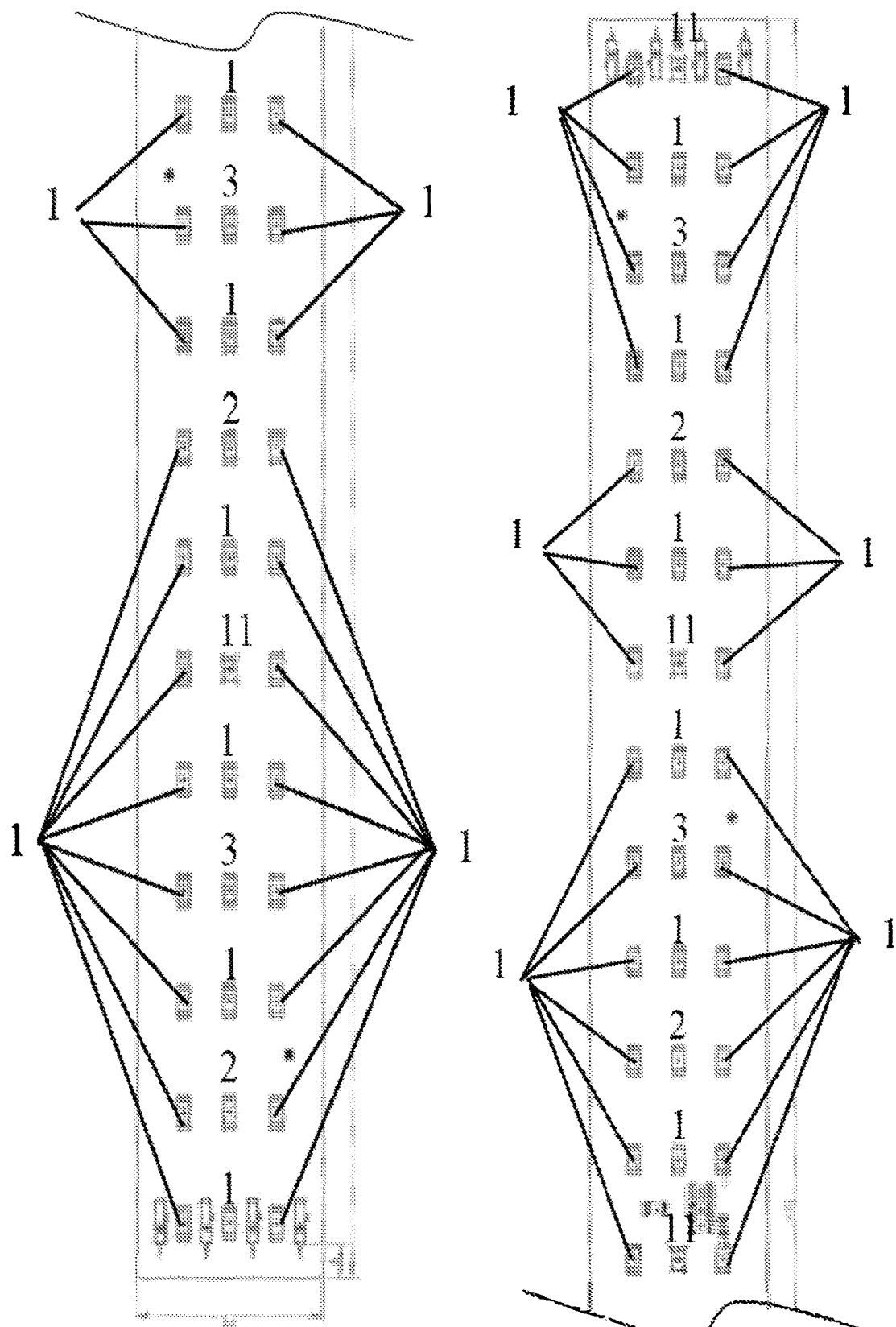
FIG. 21: Scheme of printed circuit of LED lighting source produced according to Example 5 fitted with LED chips
Figure 22:
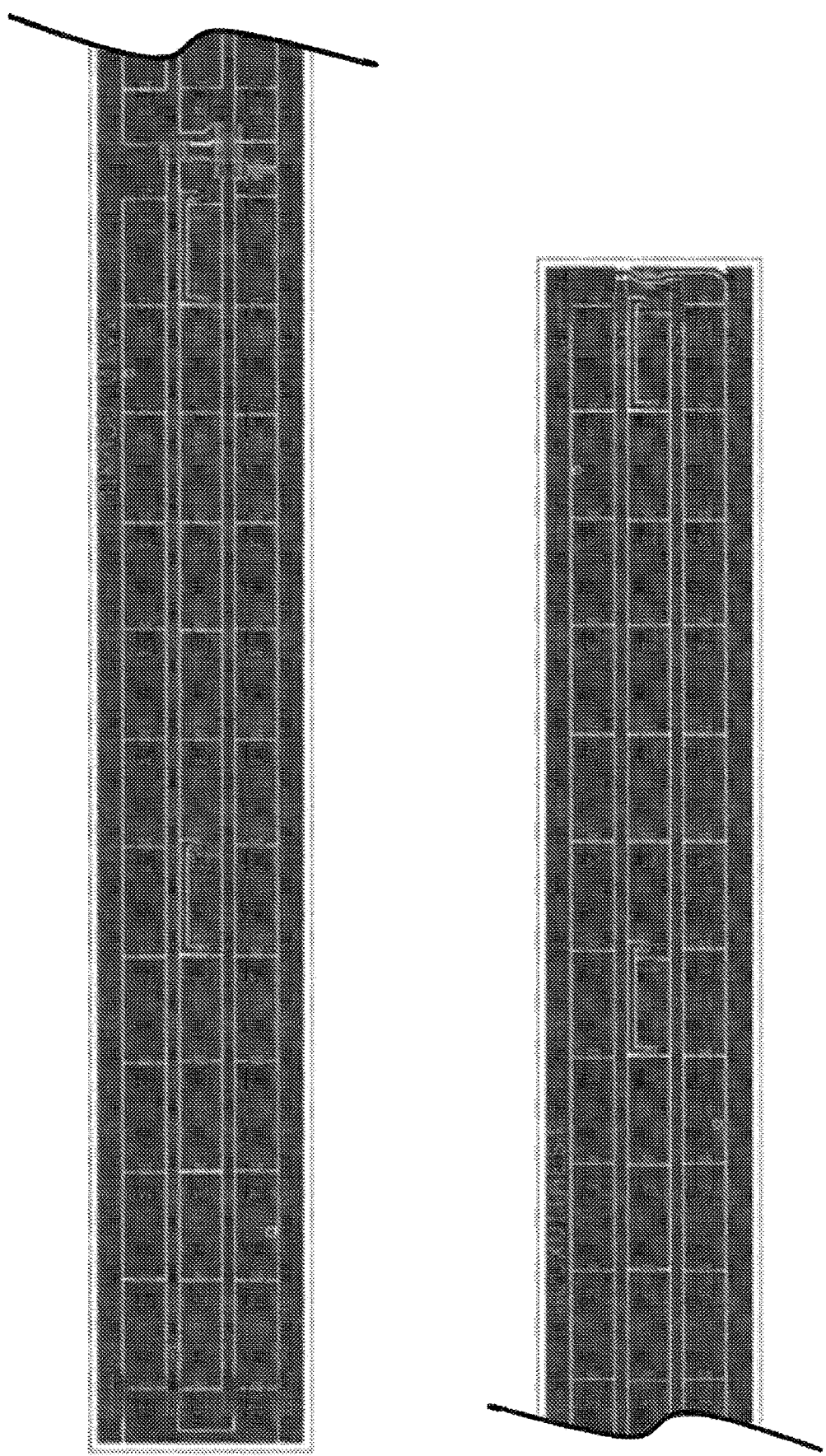
FIG. 22: Scheme of printed circuit of LED lighting source produced according to Example 5 fitted with LED chips FIGS. 23A & B: Scheme of connection of LED lighting source produced according to Example 5
Figure 23:
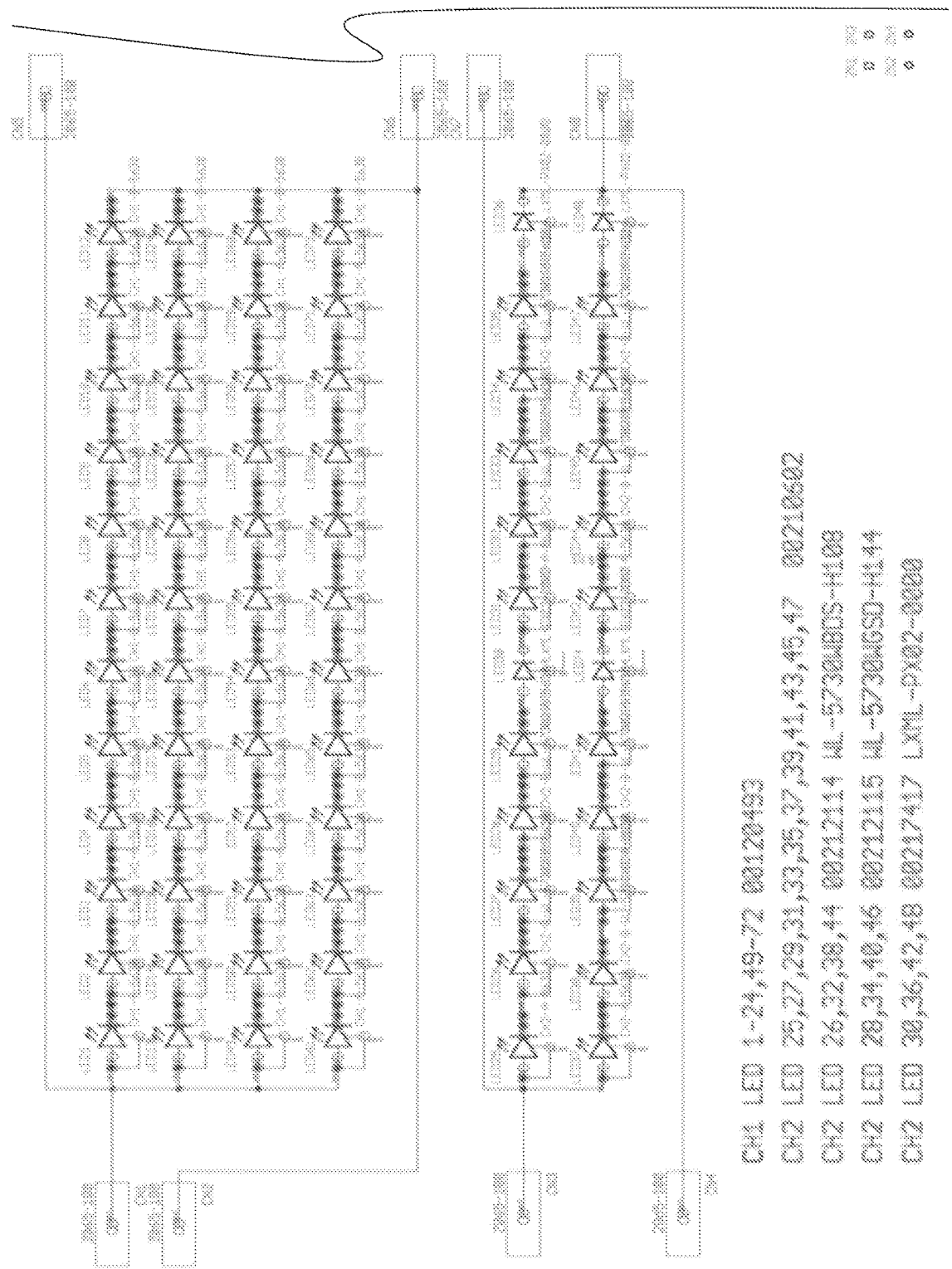
Figure 23:
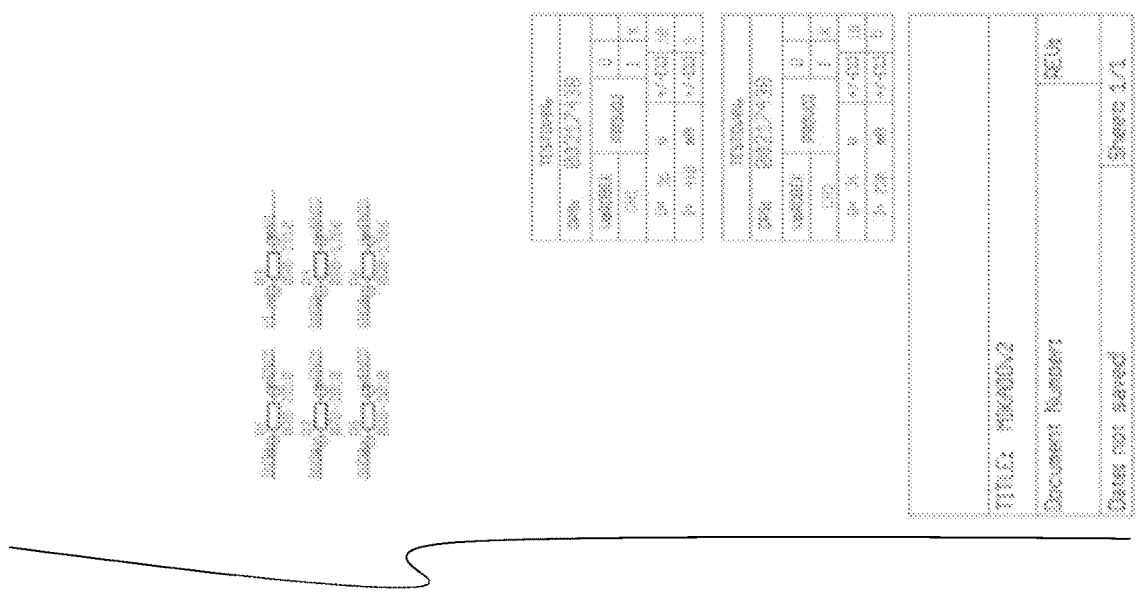
Figure 24:
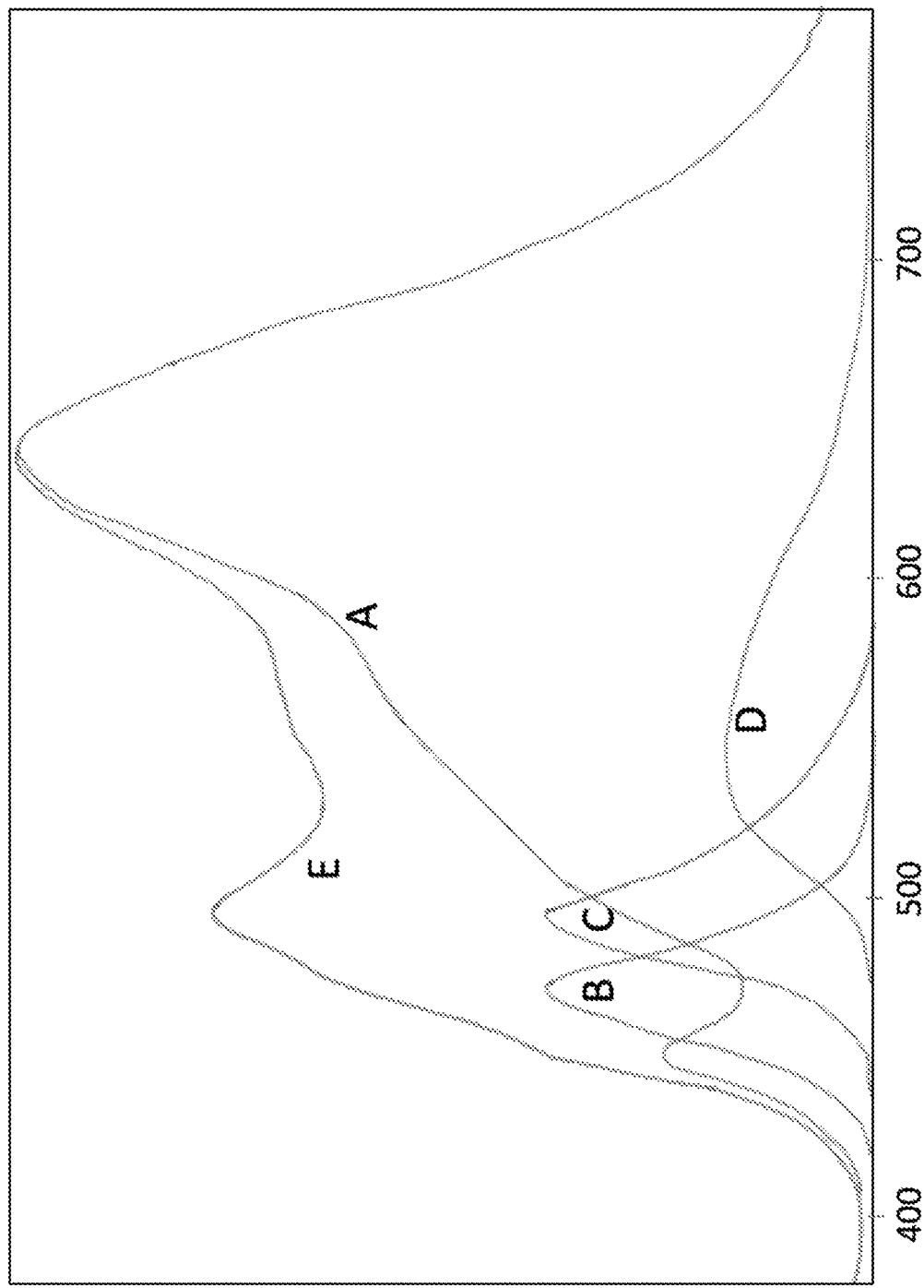
FIG. 24: Graph of spectra of all light sources of used LED chips, A-white LED chip 2700, B-blue LED chip, C-turquoise LED chip, D-PC lime LED chip, E—LED lighting source according to Example 6
Figure 25:
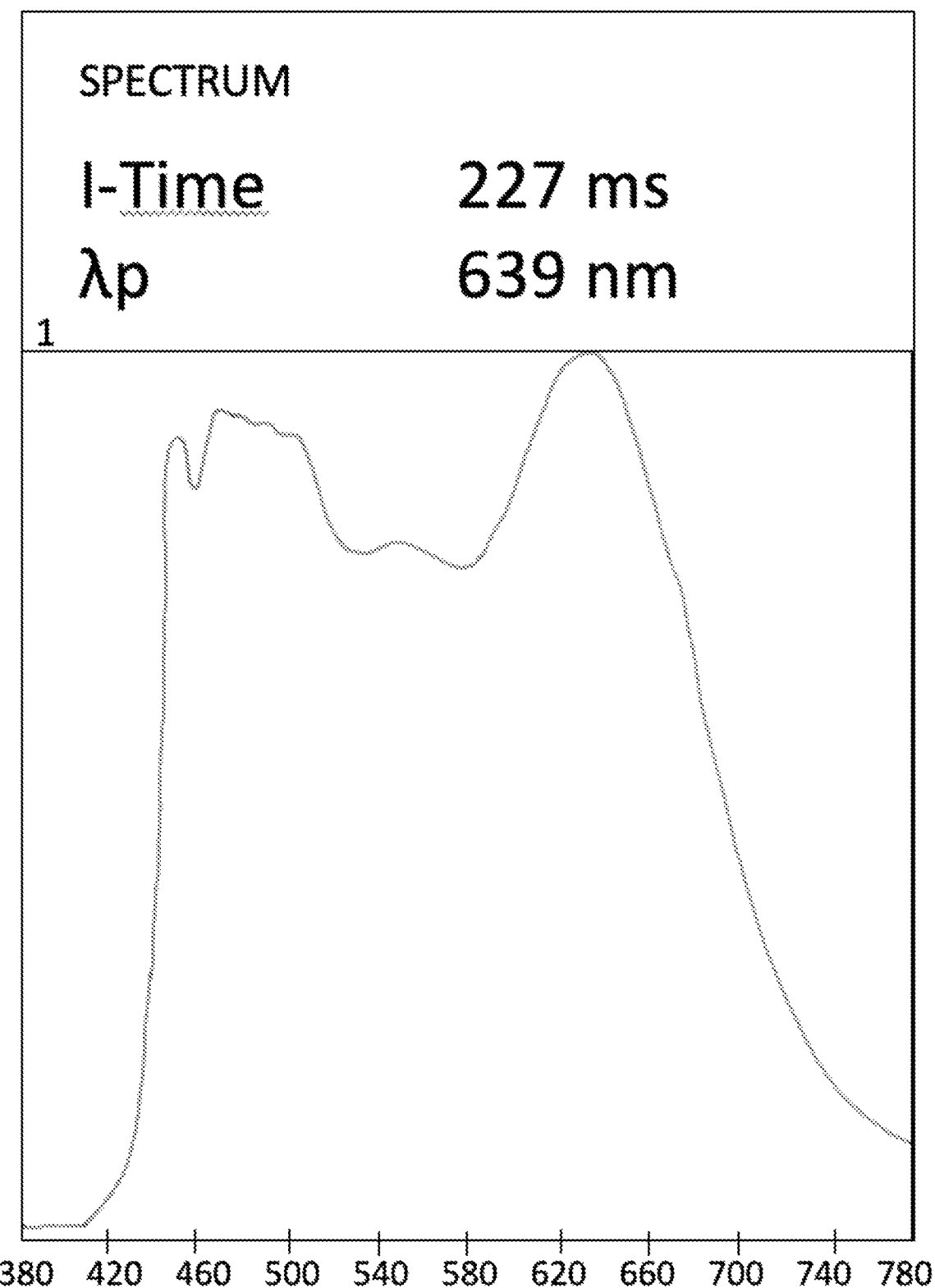
FIG. 25: Spectrofotometric spectrum emitted by cognitive LED lighting source according to Example 4

In a Prague school—Gymnázium Na Pražačce (GNP), equipment of LED lighting to improve cognitive performance according to Example 1 was installed in a part of the building. Due to the blue spectral component of light, particularly cognitive performance of the students was facilitated in the teaching rooms. Other monitored parameters were for example concentration, attention, reaction time, retention and thought rate, recalling from memory, physical performance, visual comfort and subjective content of the students and the teachers—overview of all the subjective parameters is shown in FIG. 20. The experiment was performed in two representative periods of time—before installation of the LED lighting and after, another school—Gymnázium u Libeňského zamku (GULZ) was selected as a control group. The experiment ran parallel in both the objects (GNP and GULZ). The experiment was assessed using two sets of specially designed psychological tests where one set of tests concentrated on objective parameters linked to the students' ability to learn, and the other set concentrated on subjective reception of the LED lighting by the students and the teachers. The results show that the students exposed to the LED lighting according to Example 1, show better study results, better health—the assessment parameters involved also monitoring of absence due to diseases and oversleep, and better satisfaction in comparison with control groups of students. The experiments are presented in examples below. All measurement were done using a spectrophotometer.

Example 7A Measurement of Illuminance

Measurement of illuminance in the working area recorded the actual light conditions in the teaching rooms during lessons. The established intensity of illuminance was comparable in all the teaching rooms in both the schools where the tests were carried out. Horizontal illuminance of forms and desks under invented and standard lighting amounts to some 800 lx, and the light falling in student's eye (ie. biologically efficient light) amounts to some 300-330 lx according to the position in the teaching room and a view direction.

Adequate illuminance of surface took effect when assessing legibility of texts on a blackboard which was similar in teaching rooms of the same size, very good. Though illuminance of surface in the teaching rooms is comparable, 25% students in reference teaching rooms assessed the space as too light, while only 6% of students had this opinion in new lighting. The difference in assessment is statistically important (T-test, n=104, p=0.01). The explanation of this effect can lay in better distribution and more balanced spectral composition of the new light.

Example 7B Measurement of Biological Efficiency

Measurement of the spectral curve showed that in spite of comparable level of illuminance, the new lighting achieved 0.47-0.36 $W/m^2$ in assessment of biological efficiency according to Brainard while the lighting in the reference teaching room only achieved some 0.25 to 0.20 $W/m^2$. This is possible thanks to the balanced spectral composition of the light with high share of the blue spectral component which is the key factor to achieve the required positive effect on cognitive performance and endurance and good synchronisation of biological clock of the organism.

Example 7C Objective Assessment—Tests on Cognitive Performance

Figure 19:
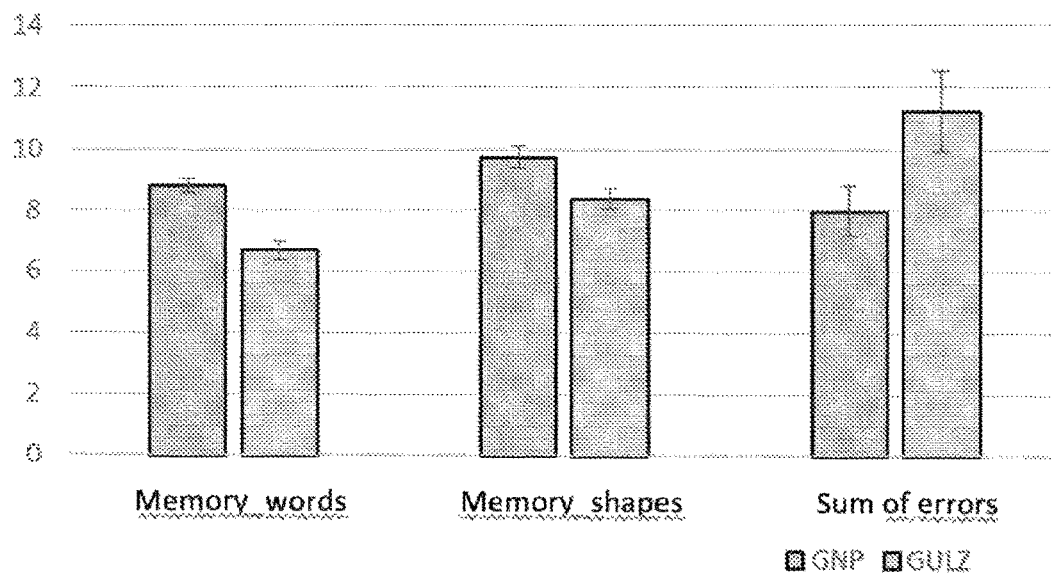
FIG. 19: Results of tests of cognitive performance–group average+average deviation. The star marks statistically significant difference according to Example 7.

Objective assessment of the effect of light was performed using tests on cognitive performance. The tests monitored concentration and short-term memory. The first stage of testing, ie. after 3 months since the lighting was installed, indicates significantly better results with the students who learn early morning in a teaching room equipped with the new cognitive lighting. These students made less mistakes in the tests (T-test, n=104, p<0.05), their recent memory was significantly better (T-test, n=104, p<0.02) compared to students of common teaching rooms. The testing results are reviewed in FIG. 19.

Example 7D Measurement of Colour Rendering Index Ra

New lighting also achieved higher colour rendering index Ra. Originally, lighting with Ra 60 was installed in all the teaching rooms in GNP as well as in the reference teaching rooms monitored in GULZ. This does not satisfy the requirements of the standard on lighting of space for long-term stay of persons, the requirement is Ra 80 and more. The new light system achieves Ra 91 which is important not only because the school focuses on art education. This was likely present in subjective assessment of students, there was a tendency to better evaluate the naturalness of the colors of the new lighting. While in the new lighting, 85% of people evaluate the skin color to be natural or relatively natural, in the original one it is only 69% of people. For averages of subjective assessment of the tested (GNP, n=51) and reference (GULZ, n=53) groups, see FIG. 20.

Example 7E Energy Savings

The new lighting was installed in some half of the teaching rooms where it replaced the original fluorescent and common savings LED lighting. The measurement was carried out for the whole object. Despite the significant increase in illuminance and, above all, the increase in lighting quality in approximately half of the space, the power consumption did not increase year-on-year. On the contrary, there was a small drop in consumption by 5% in the last quarter of the year.

Example 7F Psychological Effect

The newly installed classroom lighting was subjectively assessed as more pleasant when compared with the common lighting (t-test, n=104, p<0.01). While lighting in reference classrooms is rated only by 32% of students as pleasant or basically pleasant, in the new installed lighting it is 53%.

LIST OF MARKS FOR TERMS 1 white LED chip
2 blue LED chip
3 turquoise LED chip
4 printed circuit of white strip
5 light strip of white chips
6 light strip of blue and turquoise chips
7 printed circuit of light strip of blue and turquoise chips
8 dimer
9 voltage multiplier
10 supply
11 yellow-green PC lime LED chip

APPLICABILITY IN INDUSTRY

A light source that stimulates the cognitive performance of a person is therefore suitable wherever there is a need for great concentration and attention.

The invention claimed is:
1. An LED lighting source to improve cognitive performance and with sun-light properties with 90% balance of maxima and minima in distribution of light energy in range 460 to 660 nm comprising:
　at least one white LED chip (1) emitting light with wavelength from 380 nm to 700 nm, and at least one monochromatic blue LED chip (2) emitting light with wavelength from 470 nm to 480 nm, wherein said LED chips are connected to an electric current source; and
　at least one monochromatic turquoise LED chip (3) emitting light with wavelength from 490 nm to 500 nm, wherein the at least one white LED chip has correlated colour temperature 3800 to 4200 K and CRI 90 to 98, the at least one monochromatic blue LED chip (2) and turquoise LED chip (3) each generate 3 to 7% of a total emitted power of the LED lighting source or a light flux from the blue LED chips (2) amount to 1 to 4% of a total light flux of the LED lighting source and a light flux of the turquoise LED chips (3) amount to 4 to 7% of a total light flux of the LED lighting source and the white LED chips provide for a main emitted power and a main light flux.

2. The LED lighting source according to claim 1 further comprising at least one PC lime LED chip (11) with radiation in range of 500 to 650 nm for green-yellow wavelengths, wherein the at least one PC lime LED chip (11) utilizes 6 to 9% in a total emitted power or 10 to 15% of a total light output of the source.

3. The LED lighting source according to claim 2 wherein the PC lime LED chip (11) comprises of blue LED chip (2) excited in range 420±5 nm covered with a luminophore.

4. The LED lighting source according to claim 1 wherein the white LED chip (1) consists of a blue LED chip (2), different than the at least one monochromatic blue LED chip (2), covered with luminophores.

5. The LED lighting source according to claim 1 wherein a ratio of output of the at least one monochromatic blue LED chip (2) and the at least one turquoise LED chip (3) is 1:1.

6. The LED lighting source according to claim 2 wherein a ratio of light output of the at least one monochromatic blue LED chip (2), and the at least one turquoise LED chip (3) and the at least one PC lime LED chip (11) is 1:2:3.

7. The LED lighting source according to claim 2 wherein the total intensity of radiation of the LED lighting source is provided from 4.5 to 7% from the at least one blue LED chip (2), from 4.5 to 8% from the at least one turquoise LED chip (3), from 6 to 10% from the at least one PC lime LED chip (11) and from 78 to 88% from the at least one white LED chip (1).

8. The LED lighting source according to claim 1 wherein the total output of the at least one monochromatic blue LED chip (2) and the total output of the at least one turquoise LED chip (3), each generate 5% of the total output of the at least one white LED chip (1).

9. The LED lighting source according to claim 1 wherein four of the at least one white LED chips (1), the at least one blue LED chip (2) and the at least one turquoise LED chip (3) are positioned on 1.25 cm of printed circuit (4, 7).

10. The LED lighting source according to claim 1 wherein four of the at least one white LED chips (1), two of the at least one monochromatic blue LED chips (2) and the at least one turquoise LED chip (3) are positioned on 1.25 cm of printed circuit (4, 7) and the at least one monochromatic blue LED chip (2) has half the output of the at least one turquoise LED chip (3).

11. The LED lighting source according to claim 1 wherein four of the at least one white LED chips (1), the at least one monochromatic blue LED chip (2) and two of the at least one turquoise LED chips (3) are positioned on 1.25 cm of printed circuit (4, 7), and the at least one turquoise LED chip (3) has half the power of the at least one monochromatic blue LED chip (2).

12. The LED lighting source according to claim 2 wherein a light output of the at least one monochromatic blue LED chip (2) amounts to 27 to 32 lm/W, a light output of the at least one turquoise LED chip (3) amounts to 63 to 66 lm/W, light output of the at least one PC lime LED chip (11) amounts to 85 to 100 lm/W, and a light output of the at least one white LED chip (1) amounts to 70 to 90 lm/W.

13. The LED lighting source according to claim 2 further comprising two channels, wherein the two channels comprise:
  a I channel comprising 20 to 80 of the at least one white LED chips (1);
  and a II channel comprising one to eight groups of the at least one monochromatic blue-turquoise PC lime LED chips, and one group of the at least one monochromatic blue-turquoise PC lime LED chips consists of only one of the at least one monochromatic blue LED chip (2), only one of the at least one one turquoise LED (3) chip, and only one of the at least one PC lime LED chip (11).

14. The LED lighting source according to claim 13 wherein the I channel comprises 40 to 60 of the at least one white LED chips and the II channel comprises four groups of the at least one monochromatic blue-turquoise PC lime LED chips.

* * * * *